(12) United States Patent
Ko

(10) Patent No.: US 7,396,544 B2
(45) Date of Patent: Jul. 8, 2008

(54) SCHISANDRIN B PREPARATION

(75) Inventor: Kam Ming Ko, Kowloon (HK)

(73) Assignee: The Hong Kong University of Science and Technology, Kowloon (HK)

( * ) Notice: Subject to any disclaimer, the term of this patent is extended or adjusted under 35 U.S.C. 154(b) by 0 days.

(21) Appl. No.: 11/696,500

(22) Filed: Apr. 4, 2007

(65) Prior Publication Data

US 2007/0191477 A1   Aug. 16, 2007

Related U.S. Application Data

(63) Continuation-in-part of application No. 11/188,021, filed on Jul. 22, 2005.

(51) Int. Cl.
*A61K 36/76* (2006.01)
(52) U.S. Cl. .................................................. 424/725
(58) Field of Classification Search ....................... None
See application file for complete search history.

(56) References Cited

U.S. PATENT DOCUMENTS

| | | | |
|---|---|---|---|
| 4,684,628 A | 8/1987 | Liu | |
| 5,484,595 A | 1/1996 | Ikeya et al. | |
| 6,242,012 B1 * | 6/2001 | Newmark et al. | 424/756 |
| 6,261,565 B1 | 7/2001 | Empie et al. | |
| 6,596,321 B1 | 7/2003 | Yan et al. | |
| 6,605,305 B2 | 8/2003 | Zhao | |
| 2002/0127189 A1 | 9/2002 | Myers et al. | |
| 2003/0008048 A1 * | 1/2003 | Winston et al. | 426/548 |
| 2005/0119337 A1 | 6/2005 | Hu et al. | |

FOREIGN PATENT DOCUMENTS

| | | |
|---|---|---|
| CN | 1415318 A | 5/2003 |
| GB | 2186572 A2 | 8/1987 |
| WO | WO00/74697 A1 | 12/2000 |

OTHER PUBLICATIONS

Junqueira et al. (Molecular Aspects of Medicine (2004), vol. 25, pp. 5-16).*
Ko et al. (Molecular and Cellular Biochemistry (2002), vol. 238, pp. 181-186).*
Pan et al. (Planta Medica (2002), vol. 68, pp. 217-220).*
Chiu, Poyee et al., "Role of Cytochrome P-450 in Schisandrin B-Induced Antioxidant and Heat Shock Responses in Mouse Liver." Life Sciences 2005, 77:2887-2895.
Ip, Siupo et al., "Methylenedioxy Group as Determinant of Schisandrin in Enhancing Hepatic Mitochondrial Glutathione in Carbon Tetrachloride-Intoxicated Mice." Biochemical Pharmacology 1997, 54: 317-9.
Ko, Kamming et al., "Protection against Carbon Tetrachloride Liver Toxicity by Enantiomers of Schisandrin B Associate". Pharmaceutical Biology 2002, 40 (4): 298-301.

Ko, Kamming et al., "Shengmai San: Traditional Herbal Medicines for Modern Times". vol. 1, 2002.
Ko, Kamming et al., "Schisandrin B and other Diebnzocyclooctadiene Lignans" In: Herbal and Traditional Medicine: Molecular Aspects of Health. Packer L, Halliwell B, Ong CN, editors. Marcel Dekker: New York, Basel, Hong Kong, 2004, pp. 289-314.
Ji, Yuxia et al., "Preparation and quality evaluation of *Schisandra chinensis* parenteral emulsion" Zhongguo Yiyuan Yaoxue Zazhi, 2004, 24(11): 713-714, China.
Du, Yingfeng et al. "Determination of deoxyschizandrin and schizandrin B in *Schisandra chinensis* and Weiganfutai tablets by RP-HPLC", Zhongcaoyao, 2004, 35 (5): 519-521, China.
He, Yanping et al. "Quantitative analysis of γ-schizandrin in Manganbao granules, A complex prescription of Chinese medicine". Zhongguo Zhongyao Zazhi, 1995, 20(9): 541-2, China.
Cui, Langui et al., "Determination of deoxyschizandrin and schisandrin B in Gengnianan tablets by HPLC", Zhongcaoyao, 2001, 32(5): 409-411, China.
Zhong, Zhaoqing et al. "HPLC determination of schizandrin B in Livoprotect tablets.". Zhongcaoyao, 1996, 27(4):215-216, China.
Lui, Fengqun et al. "Simultaneous determination of schizandrin A and B in Gandeining pill by HPLC", Zhongguo Zhongyao Zazhi, 2000, 25(3): 157-158, China.
Tian, Gengcun et al. "The preparation, pharmacology and clinical application of Shengmaisan" Chinese Traditional Patent Medicine, 2000; 22(2): 162-165.
Ko, Kamming et al., "Protective Effect of a Lignan-enriched Extract of *Fructus schisandrae* on Physical Exercise Induced Muscle Damage in Rat", Phytotherapy Research, 1996; 10:450-452.
Panossian et al., "Effects of heavy physical exercise and adaptogens on nitric oxide content in human saliva", Phytomedicine, 1999, 6 (1): 17-26.
Chiu, Poyee et al., "Chronic schisandrin B treatment improves mitochondrial antioxidant status and tissue heat shock protein production in various tissues of young adult and middle-aged rats", Biogerontology, 2006, 7:199-210.
Chiu, Poyee et al., "(−) Schisandrin B is more potent than its enantiomer in enhancing cellular glutathione and heat shock protein production as well as protecting against oxidant injury in H9c2 cardiomyocytes" Molecular and Cellular Biochemistry, 2006, 289:185-191.
Chiu, Poyee et al., "Effects of Schisandrin B Enantiomers on Cellcular Glutathione and Menadione Toxicity in AML12 Hepatocytes", Pharmacology, 2006, 77:63-70.

* cited by examiner

*Primary Examiner*—Susan Coe Hoffman
(74) *Attorney, Agent, or Firm*—Ryan A. Schneider, Esq.; Troutman Sanders LLP

(57) ABSTRACT

The present invention provides a composition (e.g., a pharmaceutical composition) for reducing aging-related mitochondrial antioxidant status changes in a subject, wherein the composition comprises Schisandrin B. The present invention further provides a composition (e.g., a pharmaceutical composition) for reducing ischemia-reperfusion injury in an aging subject, wherein the composition comprises Schisandrin B. Also provided are methods for reducing aging-related mitochondrial antioxidant status changes and/or for reducing ischemia-reperfusion injury in an aging subject using the same.

6 Claims, 7 Drawing Sheets

(i)

(ii)

(iii)

(i)

(ii)

(iii)

SCHISANDRIN B PREPARATION

RELATED APPLICATIONS

The present application claims the priority of U.S. patent application Ser. No. 11/188,021, filed Jul. 22, 2005, which is herein incorporated in its entirety.

TECHNICAL FIELD

The present invention relates to preparations comprising Schisandrin B, to methods for making the preparations, and to methods for prevention and/or treatment of heart disease or other conditions using the preparations.

BACKGROUND OF THE INVENTION

Physical exercise is generally beneficial to health by enhancing body metabolism and improving heart-lung function as well as muscle endurance. One fact that is unknown to many people is the potential harmful effect produced by unaccustomed exercise due to the insufficiency in heart-lung function. When the heart-lung function is adequate for the exercise or the loss of body fluid from profuse sweating is not quickly replenished, the muscle may be injured and the heart-lung function may suffer instead of becoming healthier after exercise.

Shengmai San (SMS), a Chinese medicine formula comprising *Ginseng* root, *Schisandra* fruit and *Ophiopogonis* root, was first cited in Chinese medical literature in 1247 AD. Traditionally, SMS, which restores blood volume and prevents myocardial infarction, is used for the treatment of excessive loss of body fluid that threatens heart failure and coronary heart disease. In terms of modem medicine, SMS can enhance adaptation to stress, transformation of nutrients and oxygen into energy, oxygenation of tissues, and prevent dehydration. All these effects are beneficial for individual performing physical exercise during sports activities. Nevertheless, current sports drinks and drugs used for the prevention and treatment of coronary heart disease are not designed for enhancing the heart-lung function, which is a crucial factor in improving physical performance and in recovery from coronary heart disease.

There is a need for a preparation that can be readily administered to an individual, preferably orally, which is capable of enhancing the heart-lung function as well as preventing and/or treating cardiovascular conditions or other conditions.

SUMMARY OF THE INVENTION

In a first aspect of the invention there is provided a preparation for treatment or prevention of a condition in a patient, said preparation comprising Schisandrin B. The preparation may be suitable for oral administration to a patient. It may be ingestible, and may be drinkable. It may be non-toxic to a patient to which it is administered. The preparation may comprise Schisandrin B isolated from plant matter, for example a *Schisandra* plant, such as *Schisandra chinensis* (*Fructus schisandrae*), or it may comprise plant matter, or an extract thereof, containing Schisandrin B, or it may comprise both. Alternatively or additionally the Schisandrin B may be synthetic, and may be produced using a chemical or biochemical synthesis process (e.g. a process involving organisms produced using recombinant, mutagenic or other methods). The Schisandrin B may be the (−) isomer. Schisandrin B may be dissolved, suspended, dispersed or emulsified in the preparation. In addition, the preparation may comprise one or more other components, for example herbal extracts, fluids, solvents (e.g. water), antioxidants, preservatives, pH control agents or other additives. These may be non-toxic. They may be pharmaceutically acceptable. The preparation may be liquid, and may be an aqueous preparation. It may be a solvent based preparation, for example an ethanolic preparation, a tincture or some other solvent based preparation. The preparation may be a drink, for example a sports drink, or it may be a pharmaceutical preparation. The pharmaceutical preparation may be a liquid, or a powder or it may be in some other form. The preparation may additionally comprise other beneficial components, for example electrolytes, salts etc. The condition may be a heart condition, or a condition of some other organs for example liver, kidney or lung. The condition may be a cardiovascular condition, myocardial damage or infarction, coronary heart disease, impaired heart-lung function, cancer, heart failure, ischaemia, viral myocarditis, septic/hemorrhagic shock, liver failure, chronic hepatitis, chronic bronchitis, gastritis, type II diabetes, toxic side effects arising from cancer chemotherapy, aging and age-related diseases such as liver and heart failure, Alzheimer's disease, Parkinson's disease, dehydration or failure of other organs. The condition may be muscle damage, for example exercise induced muscle damage.

In one embodiment the preparation comprises saponins (e.g. ginsenosides derived from *Ginseng*), and lignans (derived from *Schisandra*), including Schisandrin B.

The saponins may be ginsenosides. The saponins may be present between about 0 and about 3%, or between about 0.6 and about 1.5% w/w or w/v. They may be present at about 0.6% w/v. The lignans may be present between about 0.05 and about 0.5%, or between about 0.1 and about 0.2% w/w or w/v. They may be present at about 0.1% w/v. Schisandrin B may be present between about 0.01 and about 0.1%, or between about 0.02 and about 0.04% w/w or w/v. It may be present at about 0.02% w/v. Each component may, independently, be present in suspension, solution or emulsion. The preparation may be an herbal preparation, and may be a sports drink.

In another embodiment the preparation comprises saponins (e.g. ginsenosides derived from *Ginseng*), and (−) Schisandrin B.

The total saponins may be present between about 5 and about 30%, or between about 15 and about 20% w/w, w/v or v/v. Schisandrin B may be present between about 15 and about 40%, or between about 25 and about 30% w/w or w/v. Each component may or may not, independently, be present in suspension, solution or emulsion. Alternatively the preparation may have no added components other than saponins and Schisandrin B. It may consist only of (−) Schisandrin B and saponins. The ratio of (−) Schisandrin B to saponins may be between about 1:5 and 5:1. The preparation may be a solid. It may be a powder, and may be a powdered preparation. The preparation may be a pharmaceutical preparation.

In a second aspect of the invention there is provided a process for making a preparation for treatment or prevention of a condition in a patient comprising combining Schisandrin B with at least one other component. At least one of the other components may be a liquid, or none of the other components may be a liquid. The Schisandrin B may be the (−) isomer. The liquid may be a solvent. It may be aqueous, and may be water. The liquid may comprise one or more of salts, electrolytes, nutrients, nutraceuticals, pharmaceuticals, drugs or other matter. The process may comprise isolating Schisandrin B prior to the combining. The process may comprise adding one or more of salts, electrolytes, nutrients, nutraceuticals, pharmaceuticals, drugs or other matter to the liquid, either before, during or after adding the Schisandrin B to the liquid. Each of the steps of adding may, independently, comprise dissolving, suspending, dispersing or emulsifying. Each may comprise agitating the liquid, for example swirling, stirring, shaking or sonicating. Each may comprise heating the liquid. The heating may be to a temperature below that required to denature or degrade the Schisandrin B, and optionally also below that required to denature or degrade other components of the preparation. The temperature may be between about 25 and 100° C.

The present invention also provides a preparation when made by one of the processes of the invention.

In a third aspect of the invention there is provided a method of treatment or prevention of a condition in a patient comprising administering to the patient a preparation according to the second aspect of the invention. The preparation may be administered in sufficient quantity over sufficient time to treat or prevent the condition. It may be administered between once per hour and once per week. The preparation may be administered as required. For example if the preparation is for the prevention of a cardiovascular condition following exercise, the preparation may be administered before, during and/or after exercise. The patient may drink or otherwise consume the preparation. The patient may be human or non-human, and may be a vertebrate. The vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, sheep, dog, cat, goat, llama, rabbit and a camel, for example.

In a fourth aspect of the invention there is provided a method of enhancing sports activities in a subject comprising administering to the subject a preparation comprising Schisandrin B. The Schisandrin B may be the (-) isomer. The preparation may be a preparation according to the present invention, as described above.

In a fifth aspect of the invention there is provided a method of treatment or prevention of a condition selected from the group consisting of a heart condition, a liver condition, a kidney condition, a lung condition, a cardiovascular condition, myocardial damage or infarction, coronary heart disease, impaired heart-lung function, cancer, heart failure, ischaemia, viral myocarditis, septic/hemorrhagic shock, liver failure, chronic hepatitis, chronic bronchitis, gastritis, type II diabetes, toxic side effects arising from cancer chemotherapy, aging and age-related diseases, liver failure, heart failure, Alzheimer's disease, Parkinson's disease, dehydration, failure of organs and muscle damage comprising administering to a subject in need thereof an effective amount of a pharmaceutical preparation comprising saponins and (-) Schisandrin B. The pharmaceutical preparation may be in the form of a powder. The method may comprise providing the pharmaceutical preparation to the subject. The subject may be a vertebrate, and the vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, cow, bull, ox, buffalo, sheep, dog, cat, goat, llama, rabbit, ape, monkey and a camel, for example. The administration may be oral administration, or it may be by inhalation. If the administration is by inhalation, the pharmaceutical preparation may be provided in an inhaler, and the step of providing the pharmaceutical preparation to the subject may comprise providing the inhaler having the preparation therein to the subject.

The present invention further provides a composition (e.g., a pharmaceutical composition) for reducing aging-related mitochondrial antioxidant status changes in a subject (e.g., an animal, including, without limitation, human), wherein the composition comprises Schisandrin B. In one embodiment, the composition may raise the level of at least one of glutathione and α-tocopherol in mitochondria. In another embodiment, the composition may increase the activity of at least one of Se-glutathione peroxidase and Mn-superoxide dismutase in mitochondria. In yet another embodiment, the composition may reduce mitochondrial reactive oxidant species generation. In still another embodiment, the composition may reduce the sensitivity of mitochondria to $Ca^{2+}$-induced mitochondria permeability transition.

The Schisandrin B may be (-) Schisandrin B, such as, isolated (including natural, synthetic, and/or semi-synthetic) (-) Schisandrin B. In one embodiment, the composition of the present invention comprises a Schisandrin B preparation, wherein the Schisandrin B preparation consists essentially of isolated (-) Schisandrin B.

Also provided is a composition (e.g., a pharmaceutical composition) for reducing ischemia-reperfusion injury in an aging subject (e.g., an animal, including, without limitation, human), wherein the composition comprises Schisandrin B. In one embodiment, the composition of the present invention comprises a Schisandrin B preparation, wherein the Schisandrin B preparation consists essentially of isolated (-) Schisandrin B.

Other features and advantages of the present invention will become apparent from the following detailed description. It should be understood, however, that the detailed description and the specific examples, while indicating the preferred embodiments of the invention, are given by way of illustration only, since various changes and modifications within the spirit and scope of the invention will become apparent to those skilled in the art from this detailed description.

BRIEF DESCRIPTION OF THE DRAWINGS

A preferred form of the present invention will now be described by way of example with reference to the accompanying drawings wherein.

† p<0.001, when compared with the respective control in different age groups; ** p<0.05; ## p<0.01, when compared with the middle-aged untreated group, using Student's t test.

Figure 5:
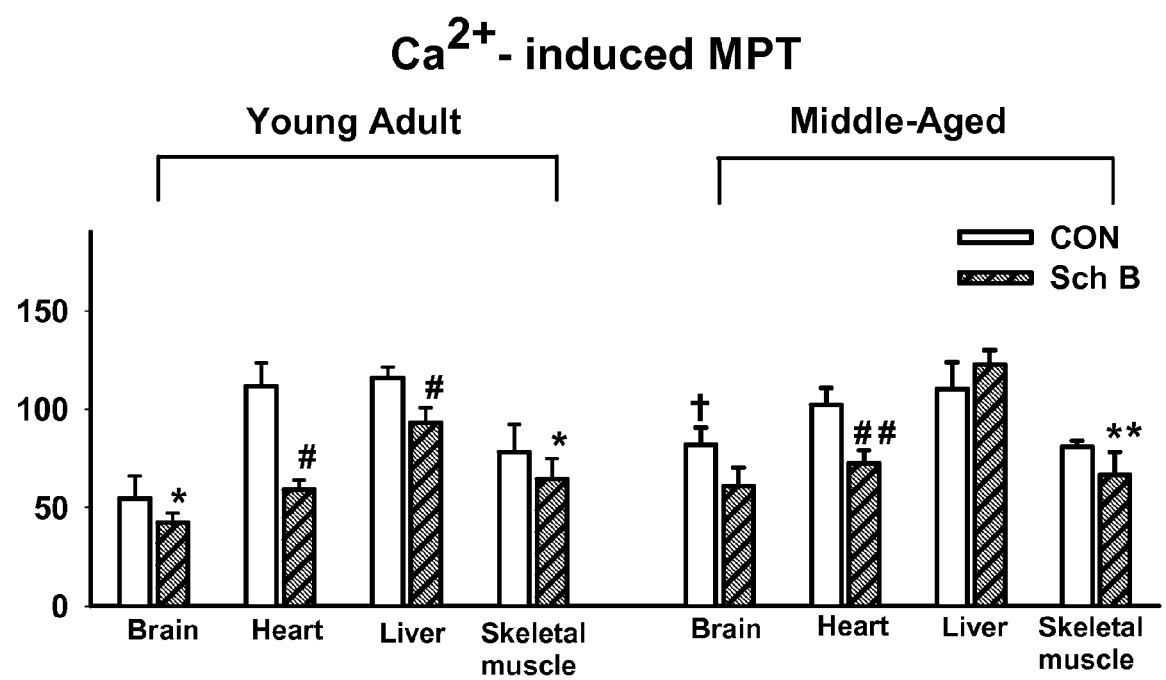

FIG. 5 shows the effects of chronic (−) Schisandrin B treatment on $Ca^{2+}$-induced mitochondrial permeability transition (MPT). Animals were treated with Sch B as described in FIG. 3. The extent of $Ca^{2+}$-induced mitochondrial permeability transition (MPT) was measured in vitro as described in Materials and Methods (Example 11). $Ca^{2+}$ was added at a final concentration of 1 μM. Data were expressed in arbitrary unit (AU). Values given are mean±S.E.M., with n=5. * p<0.05; # p<0.01; † p<0.001, when compared with the respective control in different age groups; ** p<0.05; ## p<0.01, when compared with the middle-aged untreated group, using Student's t test.

Figure 6:
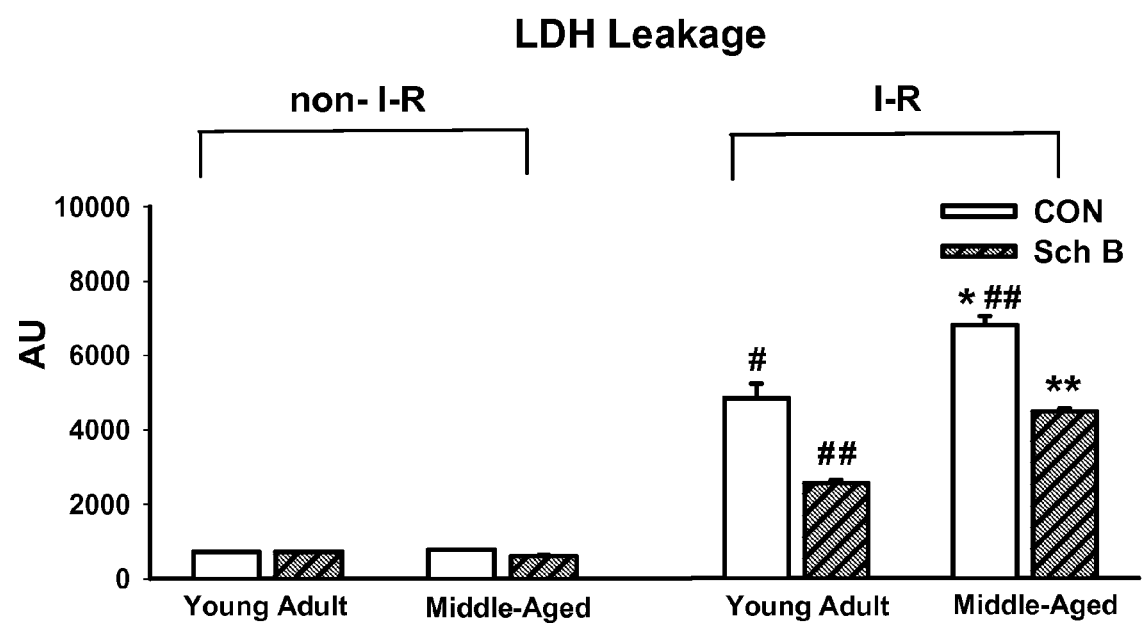

FIG. 6 depicts the effects of chronic Sch B treatment on myocardial ischemia-reperfusion (I-R) injury in young and middle-aged rats. Animals were orally treated with Sch B at a daily dose of 10 mg/kg for 35 days. Isolated hearts prepared from control or Sch B-pretreated animals were subjected to 40 min of ischemia followed by 20 min of reperfusion. The extent of LDH leakage was measured as described in Materials and methods. Data were expressed in arbitrary unit (AU). Values given are mean±S.E.M., with n=5. # significantly different from the young adult control (CON) non-I-R group; ## significantly different from the young CON I-R group; * significantly different from the middle-aged CON non-I-R group; ** significantly different from the middle-aged CON I-R group.

DETAILED DESCRIPTION OF THE PREFERRED EMBODIMENTS

As used herein and in the appended claims, the singular forms "a," "an," and "the" include plural references, unless the content clearly dictates otherwise. Thus, for example, reference to "a Schisandrin B preparation" includes a plurality of such Schisandrin B preparations and equivalents thereof known to those skilled in the art, and reference to "the saponin" is a reference to one or more saponins and equivalents thereof known to those skilled in the art, and so forth. All publications, patent applications, patents, and other references mentioned herein are incorporated by reference in their entirety.

Schisandrin B may be isolated using a process comprising:
extracting plant matter containing Schisandrin B with a solvent to produce an extract; and
purifying the extract to isolate Schisandrin B.

The plant matter may comprise one or more of leaves, flowers, seeds, stems, stalks, roots, fruit or other parts of a plant, or a combination of these. The plant matter may be dried before the extracting, and may be powdered. The plant may be any plant species which comprises Schisandrin B, for example a Schisandra plant, such as Schisandra chinensis (Fructus schisandrae). The step of extracting may comprise any of the known solvent extraction processes, including washing, boiling, refluxing, Soxhlet extraction, supercritical fluid extraction etc., or a combination of such methods. The washing may be at a convenient temperature up to the boiling point of the solvent, providing that it is not at a sufficient temperature and/or time to degrade the Schisandrin B. The solvent may be aqueous or organic. The solvent may be a supercritical fluid, such as supercritical carbon dioxide. The step of purifying may comprise any of the known methods for doing so, including column chromatography, preparative HPLC (normal phase or reverse phase), preparative GC, preparative GPC, recrystallisation or a combination of these.

The process may also comprise resolving of Schisandrin B into (+) Schisandrin B and (−) Schisandrin B. The resolution may comprise fractional crystallisation, chiral chromatography or some other suitable method.

The Schisandrin B isolated by the above process may be a mixture of isomers, or may be a single isomer. The single isomer may be (+) Schisandrin B or (−) Schisandrin B. The inventors of the present invention found that (−) Schisandrin B is a more potent and less cytotoxic compound than (+) Schisandrin B (see, for example, Examples 2, 3, and 5). In various preferred embodiments of the present invention, isolated (including natural, synthetic, or semi-synthetic) (−) Schisandrin B may be used in the manufacturing of the composition of the present invention.

The inventors have demonstrated the antioxidant properties of SMS, of which Schisandra is the antioxidant determinant herb. In studies examining the effect of Schisandra on physical performance in thoroughbred horses, it was found that Schisandra could improve the heart-lung function as well as physical performance during running exercise. Serum lactic acid was reduced and the serum glucose was increased in Schisandra-treated horses. In addition, muscle damage in poorly performing horses appeared to be reversed with Schisandra treatment. Recently the present inventors have discovered the protective effect of a lignan-enriched extract of Schisandra on physical exercise-induced muscle damage and free radical-induced myocardial damage in rats.

While ginsenosides from Ginseng have long known for their cardioprotective effects, recent studies by the inventor have shown that Schisandrin B, a dibenzocyclooctadiene derivative isolated from Schisandra, plays a pivotal role in protecting the ischemic heart by enhancing the mitochondrial glutathione antioxidant status and heat shock protein expression.

Results obtained from recent clinical studies indicated that SMS could improve clinical symptoms in patients suffering from coronary heart disease, viral myocarditis, septic/hemorrhagic shock as well as respiratory disorders. In combination with other herbs, contemporary clinical applications of SMS involve the treatment of chronic bronchitis, gastritis, type II diabetes and management of toxic side effects arising from cancer chemotherapy.

The inventors have also demonstrated the generalized organ protection (liver, heart, brain and skeletal muscle) afforded by SMS and Schisandra-derived lignans. Schisandra-derived lignans were found to be the activity determinant herb in the formula. Over the past few decades, the pharmacological activities of Schisandra or its lignan components have been extensively studied. Early evidence indicated that Schisandra could enhance heart-lung function and the body resistance to non-specific stimuli. Schisandra-derived lignans were found to produce beneficial effect on liver functions, particularly in enhancing the detoxification of xenobiotics and the regeneration of liver. Later studies also demonstrated their central nervous system modulating effect, anti-carcinogenic activity as well as cardioprotective action. The abilities of Schisandra-derived lignans to increase body resistance and suppress hepatocarcinogenesis and HIV infection illustrate much of their Qi-invigorating action in defending the body against exogenous challenges. The ability of Schisandra-derived lignans (such as Schisandrin B) to enhance mitochondrial glutathione antioxidant status and stimulate ATP generation represents an unique molecular mechanism involved in organ protection. Given the mitochondrial decay in aging, the ability of Schisandra-derived lignans/Schisandrin B to maintain mitochondrial functional integrity may retard the aging process and delay the onset of age-related diseases such as liver and heart failure, Alzheimer's disease, and Parkinson's disease. The inventors have described the use of Schisandrin B in protecting against liver toxicity in Chiu, P. Y., Tang M. H., Mak D. H. F., Poon M. K. T. and Ko K. M., "Hepatoprotective mechanism of Schisandrin B: Role of mitochondrial glutathione antioxidant status and heat shock proteins", *Free Radical Biology & Medicine* Vol. 35, No. 4, pp. 368-380 (2003), the contents of which are incorporated herein by cross-reference.

Accordingly the inventors have designed an SMS-based and *Schisandra* lignan-enriched herbal preparation for generalized organ protection having the following composition: saponins (for example 0.6-1.5%), and Lignans (e.g. derived from *Schisandra*) (for example 0.1-0.2%), wherein the lignans include Schisandrin B (for example 0.02-0.04%).

Saponins are a class of plant glycosides, and those derived from *Ginseng* are designated ginsenosides. The herbal preparation may comprise up to about 3% saponins, or may have up to 2, 1.5, 1 or 0.5% saponins, or between about 0 and about 3%, or between about 0 and 2, 0 and 1.5, 0 and 1, 0 and 0.5, 0.5 and 3, 0.5 and 2, 1 and 3, 1 and 2, 0.5 and 1.5, 0.6 and 1.5, 0.3 and 1, 0.4 and 0.8, 0.5 and 0.7, or 0.5 and 1% saponins, and may have about 0.1, 0.2, 0.3, 0.4, 0.45, 0.5, 0.55, 0.6, 0.65, 0.7, 0.75, 0.8, 0.9, 1, 1.1, 1.2, 1.3, 1.4, 1.5, 1.6, 1.7, 1.7, 1.8, 1.9, 2, 2.5 or 3% saponins w/w or w/v. It may comprise up to about 0.5% lignans, or up to about 0.4, 0.3, 0.2 or 0.1% lignans, or between about 0.05 and about 0.5%, or between about 0.05 and 0.4, 0.05 and 0.25, 0.05 and 0.15, 0.07 and 0.13, 0.08 and 0.12, 0.09 and 0.11, 0.1 and 0.4, 0.1 and 0.3, 0.1 and 0.2, 0.2 and 0.5 or 0.2 and 0.4% lignans, and may comprise about 0.05, 0.06, 0.07, 0.08, 0.09, 0.1, 0.11, 0.12, 0.13, 0.14, 0.15, 0.2, 0.25, 0.3, 0.35, 0.4 or 0.5% lignans w/w or w/v. It may comprise up to about 0.1% Schisandrin B, or up to about 0.08, 0.05, 0.04 or 0.03% Schisandrin B, or between about 0.01 and abut 0.1%, or between about 0.01 and 0.05, 0.01 and 0.04, 0.01 and 0.03, 0.015 and 0.025, 0.018 and 0.022, 0.019 and 0.021, 0.02 and 0.1, 0.02 and 0.5, 0.02 and 0.04%, and may comprise about 0.01, 0.015, 0.016, 0.017, 0.018, 0.019, 0.02, 0.021, 0.022, 0.023, 0.024, 0.025, 0.03, 0.035, 0.04, 0.045, 0.05, 0.06, 0.07, 0.08, 0.09 or 0.1% Schisandrin B or may comprise more than 0.1% Schisandrin B. The Schisandrin B may be the (−) isomer. An example of a herbal preparation as described above comprises: saponins (about 0.6%), and lignans (e.g. derived from *Schisandra*) (about 0.1%), wherein the lignans include Schisandrin B (about 0.02%). The herbal preparation may be aqueous. The saponins may be ginsenosides.

An SMS-based pharmaceutical preparation with the following composition for the prevention and treatment of coronary heart disease was also designed: total saponins, for example 15-20% and (−) Schisandrin B, for example 25-30%.

The saponins may comprise ginsenosides. Ginsenosides are steroid-like compounds, triterpene saponins, found exclusively in *Panax* species. The total saponins may be between about 5 and about 30%, or between about 5 and 25, 5 and 20, 5 and 15, 10 and 30, 15 and 30, 20 and 30, 15 and 25 or 15 and 20% w/w or w/v, and may be about 5, 10, 15, 16, 17, 18, 19, 20, 25 or 30% w/w or w/v. The amount of (−) Schisandrin B may be between about 15 and about 40%, or between about 15 and 35, 15 and 30, 15 and 25, 20 and 40, 25 and 40, 25 and 35, 25 and 30 or 20 and 30% w/w or w/v, and may be about 15, 20, 25, 26, 27, 28, 29, 30, 35 or 40% w/w or w/v.

Each of the above preparations may be aqueous. They may additionally comprise well commonly used electrolytes and/or other excipients e.g. herbal extracts, fluids, solvents, antioxidants, preservatives, salts, nutrients, nutraceuticals, pharmaceuticals, drugs, pH control agents etc.

The preparation may have no added components other than saponins and Schisandrin B. It may consist only of (−) Schisandrin B and saponins. The ratio of (−) Schisandrin B to saponins may be between about 1:5 and about 5:1, or between about 1:5 and 2:1, 1:5 and 1:1, 1:5 and 1:2, 1:5 and 1:3, 1:2 and 5:1, 1:1 and 5:1, 2:1 and 5:1, 3:1 and 5:1, 1:4 ad 4:1, 1:3 and 3:1, 1:2and 2:1, 1:1.5 and 1.5:1 or 2:1 and 1.25:1, or may be greater than about 5:1 or less than about 1:5 and may be about 1:5, 1:4, 1:3, 1:2, 1:1.5, 1:1.25, 1:1, 1.25:1, 1.5:1, 2:1, 3:1, 4:1 or 5:1 or may be some other ratio. The preparation may be a solid. It may be a powder, and may be a powdered preparation. It may be a paste.

A process for preparing a preparation according to the present invention comprises:
  preparing a saponin-containing extract;
  preparing a lignan-containing extract, which also contains Schisandrin B; and
  combining the saponin-containing extract and the lignan-containing extract.

The saponin-containing extract may be a ginsenoside-containing extract. It may be prepared by extracting appropriate plant material with a solvent. The plant material may comprise one or more herbs, or part thereof, optionally dried and/or powdered. Suitable herbs include *Panax ginseng* and *Ophiopogon japonica*. The solvent may be aqueous, and may be acidic. It may be acidified with a suitable acid to a weakly acidic pH. The extraction may comprise boiling the solvent with the plant material therein, or it may comprise extracting the plant material with the solvent using a Soxhlet apparatus, or it may use some other method. This extraction may produce an initial extract, which may be used as the saponin-containing extract or may be treated further as described below.

Unwanted material may, if required, be removed from the initial extract by precipitation with ethanol followed by filtration, concentration and redissolution. Thus the initial extract, after filtration, may be concentrated by evaporation of at least part of the solvent before the precipitation with ethanol. The filtrate may be concentrated by evaporation of at least part of the solvent, and may be concentrated to a paste. It may then be dissolved in water to produce the saponin-containing extract.

The lignan-containing extract may be produced by extraction of herbal material from *Schisandra chinensis*, or a part thereof. The herbal material may be dried and/or powdered before the extraction. The extraction may use supercritical fluid extraction, or may employ solvent extraction, for example into an alcoholic solvent. Solvent extraction may be into methanol or ethanol, although if the preparation is to be consumed by or administered to a subject, particularly a human subject, ethanol may be preferred. Similarly, if supercritical fluid extraction is used, the extract may be taken up into a solvent, such as an alcohol. Again, methanol and ethanol are suitable solvents, however if the preparation is to be consumed by or administered to a subject, particularly a human subject, ethanol may be preferred.

The saponin-containing extract and the lignan-containing extract may be combined in a ratio appropriate to produce a preparation with the required amounts of saponins, lignans and (−) Schisandrin B. The ratio may be between about 10:1 and 15:1, or some other appropriate ratio. The combined extracts may then be pH adjusted to about neutral pH. This may use an acid, a base or a buffer, as appropriate.

Schisandrin B may be extracted from *Schisandra chinensis* using solvent extraction (e.g. Soxhlet or repeated extraction) into a liquid solvent, e.g, water or an aqueous solution, or an alcohol such as ethanol, methanol, isopropanol, or some other suitable solvents. This may be conducted at reflux temperature or at room temperature, or at some other temperature, depending on the nature of the solvent, and may be for example between about 10 and 100° C., or between about 20 and 100, 40 and 100, 60 and 100, 10 and 80, 40 and 80, 10 and 30, 10 and 20 or 30 and 50° C., and may be at about 10, 20, 30, 40, 50, 60, 70, 80, 90 or 100° C.

Alternatively it may be extracted into a supercritical fluid, for example supercritical carbon dioxide. The temperature may be greater than about 30° C., or greater than about 40, 50, 60, 70 or 80° C., or may be between about 30 and about 100, or between about 40 and 100, 60 and 100, 30 and 60, 40 and 60, 50 and 70, 55 and 65 or 58 and 72° C., and may be about 30, 40, 50, 55, 60, 65, 70, 75, 80, 90 or 100° C. The pressure may be greater than about 10 MPa, or greater than about 20, 30, 40, 50, 60, 70 or 80 MPa, or may be between about 10 and about 80 MPa, or between about 10 and 70, 10 and 50, 10 and 30, 30 and 80, 50 and 80, 20 and 70, 30 and 60, 40 and 60, 45 and 55 or 50 and 55 MPa, or may be about 10, 20, 30, 40, 45, 50, 55, 60, 65, 70 or 80 MPa, or may be greater than 80 MPa. It may be for example about 7500 psi (about 52 MPa). The restrictor may be kept at between about 50 and 100° C., or between about 60 and 100, 80 and 100, 50 and 70, 70 and 90 or 75 and 85° C., and may be kept at about 50, 60, 70, 80, 90 or 100° C. The flow rate may be between about 1 and about 10 ml/min, or between about 1 and 5, 1 and 2, 2 and 10, 5 and 10, 1 and 3, 1.5 and 2.5 or 1.8 and 2.2 ml/min. The dynamic extraction may be maintained for at least about 10 minutes, or at least about 15, 20, 25, 30, 34, 40 or 45 minutes, or between about 10 and about 40 minutes, or between about 10 and 30, 10 and 20, 20 and 40, 30 and 40, 25 and 35 or 28 and 32 minutes, and may be maintained for about 10, 15, 20, 25, 30, 34 or 40 minutes or longer. The extract may be collected in a solvent, for example water or an alcohol such as ethanol, methanol or isopropanol to produce a Schisandrin extract.

The extract, optionally in the solvent, may be combined with a second herbal extract, e.g. a saponin-containing extract. Thus an herb (e.g. *Panax ginseng* and/or *Ophiopogon japonica*) or part thereof, optionally powdered, optionally dried, may be extracted by a suitable solvent, e.g. an alcohol (ethanol, methanol, isopropanol etc.) or water. The solvent may be pH adjusted to an acidic pH, e.g. between about 2 and about 7, or between about 3 and 7, 4 and 7, 2 and 5, 3 and 6, 3 and 5, 2 and 4, 2.5 and 3.5 or 3 and 3.5. This may be achieved by addition of a suitable acid e.g. citric acid. The extraction may be at any temperature up to the boiling point of the solvent, and, depending on the solvent, may be for example greater than about 30° C., or greater than about 40, 50, 60, 70 or 80° C., or may be between about 30 and about 100, or between about 40 and 100, 60 and 100, 30 and 60, 40 and 60, 50 and 70, 90 and 100 or 95 and 100° C., and may be about 30, 40, 50, 55, 60, 65, 70, 75, 80, 90 or 100° C. The extraction may be for at least about 0.5 hours, or at least about 1, 1.5, 2, 2.5, 3, 4 or 5 hours, or for between about 0.5 and about 5 hours, or between about 1 and 5, 2 and 5, 3 and 5, 0.5 and 3, 0.5 and 1, 1 and 3, 1.5 and 2.5 or 1.8 and 2.2 hours, and may be for about 0.5, 1, 1.5, 1.6, 1.7, 1.8, 1.9, 2, 2.1, 2.2, 2.3, 2.4, 2.5, 3, 3.5, 4, 4.5 or 5 hours or longer. The extraction may be performed once, or more than once, e.g. 2, 3, 4 or 5 times or more than 5 times. The extract may be reduced in volume by evaporation, optionally at elevated temperature and/or reduced pressure (e.g. in a rotary evaporator), to between about 0.1 and about 0.5 of its volume, or between about 0.1 and 0.3 or 0.3 and 0.5, or 0.2 and 0.4 or 0.3 and 0.4 of its volume, or to about 0.1, 0.2, 0.25, 0.3, 0.33, 0.35, 0.4, 0.45 or 0.5 of its volume. The extract may be treated with a second fluid e.g. ethanol or isopropanol, in order to precipitate undesirable materials, which may be removed by filtration, centrifugation or other suitable process to isolate a liquid portion. The liquid portion may then be evaporated to a paste, optionally at elevated temperature and/or reduced pressure (e.g. in a rotary evaporator) and redissolved or resuspended in a suitable liquid, e.g. water to provide the second herbal extract.

The ratio of the second herbal extract to the Schisandrin extract may be between about 20:1 and about 1:1, or between about 20:1 and 5:1, 20:1 and 10:1, 20:1 and 15:1, 15:1 and 1:1, 10:1 and 1:1, 15:1 and 5:1, 15:1 and 10:1, 12:1 and 10:1 or 12:1 and 11:1, and may be about 20:1, 18:1, 16:1, 14:1, 13:1, 12:1, 11.5:1, 11:1, 10.5:1, 10:1, 8:1, 6:1, 4:1, 3:1, 2:1 or 1:1, and may be for example about 750:67, on a w/w or v/v basis. The combination of second herbal extract and Schisandrin extract may be adjusted to a pH between about 6 and 8, or between about 6.5 and 8, 7 and 8, 7 and 7.5, 6.5 and 7.5, 6.8 and 7.2, 6 and 7.5 or 6 and 7, and may be adjusted to a pH about 6, 6.5, 6.6, 6.7, 6.8, 6.9, 7, 7.1, 7.2, 7.3, 7.4, 7.5 or 8. The adjusting may use a strong acid, for example hydrochloric acid, which may be dilute, for example between about 0.1 and about 2M, or between about 0.1 and 1, 0.1 and 0.5, 0.5 and 1 or 1 and 2M, or may be about 0.1, 0.2, 0.3, 0.4, 0.5, 0.6, 0.7, 0.8, 0.9, 1, 1.5 or 2M. Alternatively the pH adjustment may use a buffer, e.g. a phosphate based buffer to achieve the desired pH. If the combination of second herbal extract and Schisandrin extract is acidic, the pH may be adjusted using base, e.g. dilute sodium hydroxide solution. The pH adjusted combination may be used as the preparation of the invention.

*Schisandra* fruit has been used as a tonic herb in Chinese medicine. It has been used for the treatment of chronic hepatitis. Schisandrin B, the most abundant dibenzocyclooctadiene derivative, has been found to be a cardio-protective principle. Recent studies by the inventors have discovered that the enantiomers of Schisandrin B ((+) Sch B and (−) Sch B) produce differential cardio-protective effect by enhancing the mitochondrial glutathione antioxidant status and heat shock protein expression. There is therefore disclosed the use of (−) Sch B as a pharmacological agent for the prevention and treatment of coronary heart disease. (our present invention is mainly related to heart protection) The inventors have found that (−) Schisandrin B is superior to (+) Schisandrin B in terms of efficacy, with respect to cardio-protection, and toxicity. Use of (−) Schisandrin B as an active nutraceutical/pharmacological ingredient may therefore be beneficial.

The following examples illustrate the present invention, which are set forth to aid in the understanding of the invention, and should not be construed to limit in any way the scope of the invention as defined in the claims.

EXAMPLES

Example 1

Extraction and Purification of (−) Schisandrin B (Sch B)

Dried powder of the *Schisandra* fruits (*Schisandra chinensis* (Turcz) Baillon) was extracted with petroleum ether. The petroleum ether extract was then subjected to silica gel column chromatography using isocratic elution with acetone:petroleum ether (5:95, v/v). The Schisandrin B-containing fractions, as detected by thin layer chromatography, were pooled, and a crude crystalline fraction was obtained. The crystalline fraction was further purified by preparative reverse-phase HPLC using Prep Nova-Pak HR $C_{18}$ (19×300 mm) column eluted by methanol:$H_2O$ (75:25, v/v). Purified (−) Schisandrin B and (+) Schisandrin B were obtained, and the chirality of (−) Schisandrin B and (+) Schisandrin B (FIG. 1) was confirmed by optical rotation measurement, with the specific rotation measured in methanol at 20° C. being −47.2° and +55.3°, respectively. HPLC analysis using chiral column (CHIRACEL OD-H, 4.6×250 mm, Diacel Chemical Industrial Ltd.) revealed the purity of each enantiomer being higher than 95%.

Physical Properties:

$C_{23}H_{28}O_6$ MW: 400.48

Rhombic crystal (methanol), mp 117-119° C.

Example 2

Time-Course of (−) Schisandrin B-Induced Increase in Cellular GSH Level in H9c2 Cells: Protection Against Oxidative Challenge by Xanthine/Xanthine Oxidase (X/XO)

Methods

Cell Culture

H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 μg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Pretreatment and Xanthine/Xanthine Oxidase-Induced Cytotoxicity

Cultured H9c2 cells were treated with (−) Schisandrin B, (+) Schisandrin B or (±) Schisandrin B (dissolved in DMSO) at 6.25 μM (0.2% DMSO final concentration) for increasing periods of time. Control cells were given the vehicle (i.e. DMSO) only. Immediately following the drug or vehicle pretreatment, the cells were challenged with a mixture of xanthine (X) (0.1 mM) and xanthine oxidase (XO) (0.4U/ml) for 4 h. The control cells were treated with the medium only. After the X/XO challenge, the medium was taken for the measurement of LDH activity, a biochemical index of cellular injury.

Measurement of Cellular GSH Level

The cells were washed twice with 0.5 ml cold phosphate-buffered saline (PBS), An aliquot (200 μl) of 3% sulfonsalicyclic acid was then added, and the mixture was incubate at 4° C. for 10 min. After centrifuging at 300 g for 15 min at 4° C., the supernatant was used for GSH measurement by an enzymatic method of Griffith (1980).

Results (−) Schisandrin B treatment at 6.25 μM caused a time-dependent increase in cellular reduced glutathione (GSH) in H9c2 cells, with the maximum stimulation occurring at 16 h post-dosing. The enhancing effect then gradually declined, with no detectable stimulatory effect at 48 h post-dosing (Table 1b).

(+) Schisandrin B or (±) Schisandrin B also produced a time-dependent increase in GSH level, with a smaller extent of stimulation than that of (−) Sch B at 16 h post-dosing (Table 1a). The beneficial effect of (−) Schisandrin B treatment became more evident after the oxidative challenged by X/XO. The (−) Schisandrin B-induced increase in GSH level was paralleled by the protection against cell injury induced by X/XO, as evidenced by the decrease in lactate dehydrogenase (LDH) leakage, with the maximum extent of protection occurring at 16 h post-dosing (TABLE 1B).

(+) Schisandrin B or (±) Schisandrin B pretreatment also produced a time-dependent protection against X/XO-induced cellular injury, with a smaller degree of protection than that of (−) Schisandrin B at 16 h post-dosing (Table 1b).

TABLE 1a

| | GSH Level (nmol/mg protein) Time Post-Dosing (h) | | | | | |
|---|---|---|---|---|---|---|
| | 0 | 4 | 8 | 16 | 24 | 48 |
| NON-X/XO | | | | | | |
| (−) Sch B | 35.8 ± 1.04 | 46.8 ± 0.88 | 54.2 ± 1.42 | 92.6 ± 1.29*** (158%) | 79.0 ± 1.48 | 54.7 ± 3.58 |
| (+) Sch B | 34.2 ± 2.41 | 38.3 ± 1.48 | 46.3 ± 0.85 | 73.9 ± 1.38*** (117%) | 66.7 ± 1.83 | 59.0 ± 2.94 |
| (±) Sch B | 38.3 ± 1.16 | 44.1 ± 3.60 | 46.2 ± 1.90 | 85.8 ± 2.57*** (124%) | 76.6 ± 0.88 | 58.8 ± 6.54 |
| X/XO | | | | | | |
| (−) Sch B | 15.9 ± 0.45 | 18.3 ± 0.57 | 20.7 ± 0.61 | 25.1 ± 1.50** (57%) | 17.8 ± 0.59 | 16.7 ± 0.63 |
| (+) Sch B | 13.9 ± 1.68 | 15.4 ± 0.55 | 16.8 ± 0.85 | 18.4 ± 0.33* (32%) | 17.2 ± 0.36 | 14.1 ± 0.53 |
| (±) Sch B | 14.5 ± 1.06 | 15.8 ± 0.49 | 16.7 ± 1.32 | 22.3 ± 0.15** (54%) | 18.9 ± 0.50 | 14.3 ± 1.04 |

Drug was added at a final concentration of 6.25 μM. Xanthine (0.1 mM) and xanthine oxidase (0.4 U/ml) (X/XO) were added in challenged condition.
Values given are mean ± S.E.M., with n = 3.
The number in parentheses is the percent increase when compared with the respective unpretreated control (i.e. 0 h).
*p < 0.05,
**p < 0.005 and
***p < 0.0005, when compared with the respective control (i.e. 0 h).

TABLE 1b

| | LDH Leakage (U/L) Time Post-Dosing (h) | | | | | |
|---|---|---|---|---|---|---|
| | 0 | 4 | 8 | 16 | 24 | 48 |
| NON-X/XO | | | | | | |
| Control | 9.14 ± 0.49 | 8.64 ± 0.46 | 7.66 ± 0.51 | 8.32 ± 0.33 | 8.16 ± 0.24 | 8.86 ± 0.12 |
| X/XO | | | | | | |
| (−) Sch B | 34.8 ± 1.13 | 26.0 ± 0.92 | 22.0 ± 0.63 | 14.2 ± 0.35*** (*78%*) | 17.5 ± 0.85 | 26.3 ± 0.41 |
| (+) Sch B | 35.7 ± 0.24 | 31.3 ± 0.71 | 25.2 ± 0.45 | 19.4 ± 0.29*** (*62%*) | 22.4 ± 1.07 | 33.5 ± 0.17 |
| (±) Sch B | 33.9 ± 0.93 | 28.7 ± 1.35 | 22.8 ± 0.45 | 15.8 ± 0.91** (*65%*) | 20.1 ± 0.76 | 29.2 ± 0.57 |

Drug was added at a final concentration of 6.25 μM. Xanthine (0.1 mM) and xanthine oxidase (0.4 U/ml) (X/XO) were added in the challenged condition.
Values given are mean ± S.E.M., with n = 3.
The italicized number in parentheses is the percent protection when compared with the unpretreated control (i.e. 0 h).
**P < 0.005 and
***P < 0.0005 when compared with the respective control (i.e. 0 h), using Student's t test.

Example 3

Cytoprotective Effect of (−) Schisandrin B on Menadione-Induced Toxicity in H9c2 Cells Methods Cell Culture H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 μg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Pretreatment and Menadione Challenge

Cultured H9c2 cells were treated with (−) Schisandrin B, (+) Schisandrin B or (±) Schisandrin B (dissolved in DMSO) at 6.25 μM (0.2% DMSO final concentration) for 16 h. Control cells were given the vehicle (i.e. DMSO) only. Immediately following the drug or vehicle pretreatment, the cells were challenged with menadione (dissolved in ethanol) at 12.5 μM (0.2% ethanol final concentration) for 4 h. The control cells were treated with the medium containing 0.2% ethanol only. After the menadione challenge, the medium was taken for the measurement of LDH activity, an biochemical index of cell injury.

Measurement of Cellular GSH Level

The cells were washed twice with 0.5 ml cold phosphate-buffered saline (PBS), An aliquot (200 μl) of 3% sulfonsalicyclic acid was then added, and the mixture was incubate at 4° C. for 10 min. After centrifuging at 300 g for 15 min at 4° C., the supernatant was used for GSH measurement by an enzymatic method of Griffith (1980).

Results (−) Schisandrin B treatment at 6.25 μM for 16 h increased cellular GSH level in H9c2 cells (Table 2). (+) Schisandrin B or (±) Schisandrin B treatment at the same dose also increased cellular GSH level, but to a smaller extent than that of (−) Schisandrin B (Table 2).

The beneficial effect of (−) Schisandrin B on H9c2 cells became more evident after the menadione challenge. (−) Schisandrin B pretreatment protected against the menadione cytotoxcity, as evidenced by the decrease in LDH leakage (Table 2). The cytoprotection was associated with an enhancement in cellular GSH level. Both (+) Schisandrin B and (±) Schisandrin B pretreatment protected against menadione cytotoxicity, but to a smaller degree than that of (−) Schisandrin B (Table 2).

TABLE 2

| | LDH (U/ml) | GSH Level (nmol/mg protein) |
|---|---|---|
| NON-MENADIONE | | |
| Control | 14.4 ± 0.40 | 34.7 ± 2.06 |
| (−) Sch B | 14.3 ± 0.29 | 64.0 ± 2.96*** (*84%*) |
| (+) Sch B | 13.5 ± 0.08 | 48.4 ± 0.60** (*41%*) |
| (±) Sch B | 14.6 ± 0.67 | 46.5 ± 2.58* (*34%*) |
| MENADIONE | | |
| Control | 30.2 ± 0.29 | 18.5 ± 0.47 |
| (−) Sch B | 20.6 ± 0.18*** (*60%*) | 33.3 ± 1.75** (*81%*) |
| (+) Sch B | 24.7 ± 0.56** (*30%*) | 24.5 ± 2.03* (*55%*) |
| (±) Sch B | 23.6 ± 0.56** (*43%*) | 28.9 ± 0.66*** (*56%*) |

The drug was added at a final concentration of 6.25 μM. Menadione was added at a final concentration of 12.5 μM for 4 h. Values given are mean ± S.E.M., with n = 3.
The italicized number in parentheses is the percent protection when compared with the menadione control.
The non-italicized number in parentheses is the percent increase when compared with the respective control (non-menadione or menadione).
*p < 0.05, p < 0.005 and p < 0.0005 when compared with the respective control, using Student's t test.

Example 4

Effect of (−) Schisandrin B on Hsp25 and Hsp70 Expression in H9c2 Cells

Methods

Cell Culture

H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 μg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Treatment

Cultured H9c2 cells were treated with (−) Schisandrin B, (+) Schisandrin B or (±) Schisandrin B (dissolved in DMSO) at 6.25 μM (0.2% DMSO final concentration) for increasing periods of time. Control cells were given the vehicle (i.e. DMSO) only.

Measurement of Heat Shock Protein Levels

Immediately following the drug treatment, the cells were washed twice with 0.5 ml cold PBS and treated with 100 μl lysis buffer containing 20 mM Tris HCl, 3 mM EGTA, 1% Triton X-100, 10% glycerol and 2 mM dithiothreitol, pH 7.5, with freshly added protease inhibitors (1 mM phenylmethylsulfonyl fluoride, 0.1 mM benzamide, 5 μg/ml leupeptin, 5 μg aproptinin and 5 μg/ml pepstain A). The mixture was incubated at 4° C. for 15 min with constant shaking. Then the cells were scraped off from the plate, and the extract was transferred to a microcentrifuge tube for centrifugation at 2,400 g for 3 min at 4° C. The resultant supernatant was used for Hsp analysis. Hsp25 and Hsp70 levels was estimated by Western blot analysis using specific antibodies (anti-Hsp25, catalog # SPA-801; anti-Hsp70, catalog # SPA-812) from StressGen (Vancouver, BC, Canada) following SDS-PAGE analysis cell lysates, using a separating gel of 10% acrylamide as described in Ip et. al. [2001]. Hsp25/27 and Hsp70 (human recombinant proteins from StressGen) and actin (bovine muscle from Sigma) were used as markers for reference. The immuno-stained protein bands were revealed by enhanced chemiluminescence reaction (Amersham ECL+) followed by the exposure to X-ray film. All immuno-blots were analyzed by densitometry, and the amounts (arbitrary units) of Hsp were normalized with reference to actin levels (arbitrary units) in the sample.

Results (−) Schisandrin B treatment at 6.25 μM caused a time-dependent increase in Hsp25 and Hsp70 levels in H9c2 cells, with the maximum stimulation occurring at 24 h post-dosing and the extent of increase in Hsp70 being more prominent (Table 3a, b).

While both (+) Schisandrin B and (±) Schisandrin B could increase Hsp25 level to a similar extent as (−) Schisandrin B, the extent of stimulation afforded by (+) Schisandrin B or (±) Schisandrin B treatment in Hsp70 levels was much smaller than that of (−) Schisandrin B (Table 3a,b).

TABLE 3a

| | Hsp 25 Level (AU) Time Post-Dosing (h) | | | | |
|---|---|---|---|---|---|
| | 0 | 8 | 16 | 24 | 48 |
| (−) Sch B | 1722 ± 99 | 1386 ± 50 | 1432 ± 83 | 1956 ± 113 (14%) | 1878 ± 108 |
| (+) Sch B | 1722 ± 99 | 1832 ± 105 | 1498 ± 86 | 2168 ± 125** (26%) | 1673 ± 97 |
| (±) Sch B | 1413 ± 76 | 1512 ± 39 | 1611 ± 93 | 1728 ± 101** (24%) | 1332 ± 77 |

TABLE 3b

| | Hsp 70 Level (AU) Time Post-Dosing (h) | | | | |
|---|---|---|---|---|---|
| | 0 | 8 | 16 | 24 | 48 |
| (−) Sch B | 465 ± 14.3 | 486 ± 16.7 | 548 ± 6.67 | 1058 ± 61*** (128%) | 556 ± 32.1 |
| (+) Sch B | 465 ± 14.3 | 576 ± 20.3 | 657 ± 13.4 | 834 ± 48.1** (79%) | 656 ± 37.8 |
| (±) Sch B | 434 ± 15.5 | 389 ± 24.7 | 652 ± 23.9 | 639 ± 23.4** (47%) | 419 ± 15.4 |

Drug was added at a final concentration of 6.25 μM. Values given are mean ± S.E.M., with n = 3. The number in the parentheses is the percent increase when compared with the unpretreated control (i.e. 0 h).
P < 0.005 and *p < 0.0005 when compared with the respective control (i.e. 0 h), using Student's t test.

Example 5

Cytotoxicity Test on (−) Schisandrin B in H9c2 Cells

Methods

Cell Culture

H9c2 cells, a permanent cell line derived from cardiac myoblasts of rat embryo, have early been characterized as a suitable model of myocardial cells [Hescheler et al. 1991]. H9c2 cells were cultured as monolayers in Dulbecco's modified Eagle's medium (GIBCO BRL) supplemented with 10% (v/v) fetal bovine serum. The medium contained glucose (4.5 g/L) and glutamine (4.5 mM), supplemented with $NaHCO_3$ (17 mM), penicillin (100 IU/ml), and streptomycin (100 μg/ml). Cells were grown under an atmosphere of 5% $CO_2$ in air at 37° C. The medium was replaced by fresh medium every 2 or 3 days. A stock of cells was grown in a 75 cm culture flask and split before confluence at a subcultivation ratio of 1:10. Cells used for experiments were seeded at a density of $3.75 \times 10^4$ cells/well on a 12-well culture plate, and the cells were grown for 24 h to about 80% confluence prior to drug treatment.

Drug Treatment

Cultured H9c2 cells were treated with (−) Schisandrin B or (+) Schisandrin B (dissolved in DMSO) at 6.25 μM (0.2% DMSO final concentration) at increasing concentrations or at increasing concentrations for 24 h. Control cells were given the vehicle (i.e. DMSO) only.

Cell Viability Measurement

Cell viability was evaluated by trypan blue staining (dead cells) and LDH leakage as well as WST staining (viable cells).

Figure 2A:
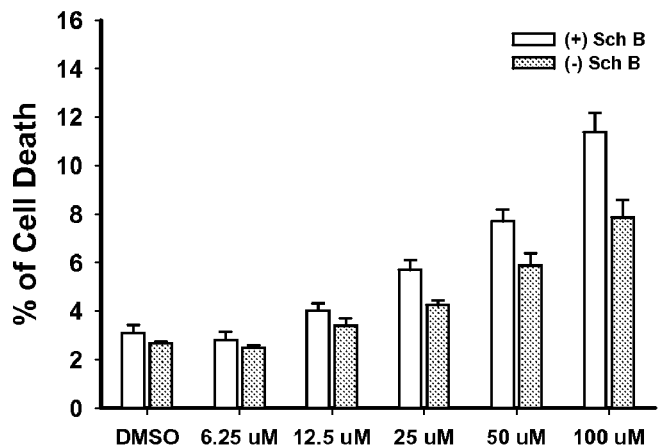
FIGS. 2A and 2B show graphs illustrating the cytotoxic effect of (-) Schisandrin B as a function of (A) dose, and (B) time.
Figure 2A:
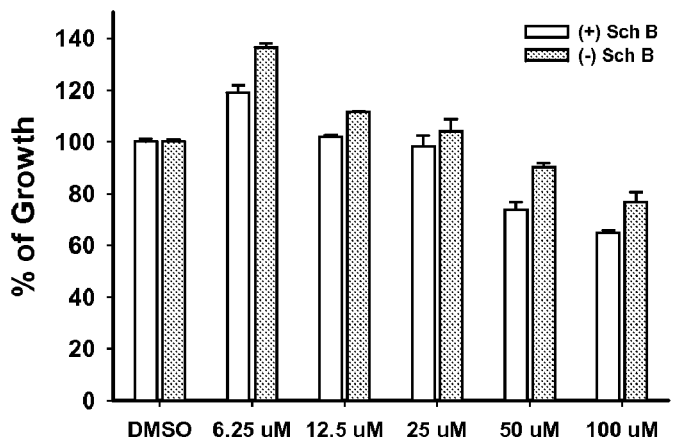
Figure 2A:
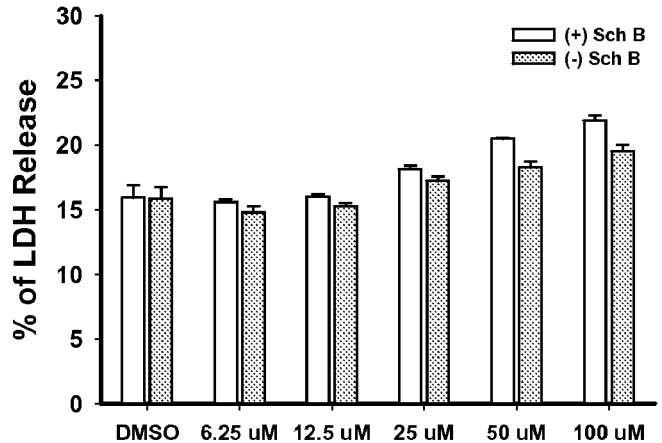
Figure 2B:
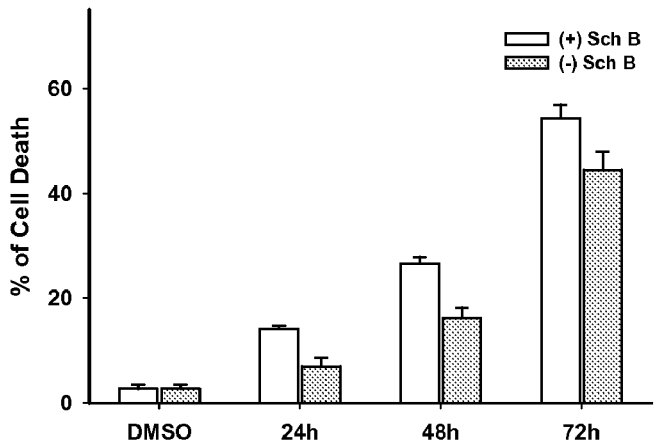
Figure 2B:
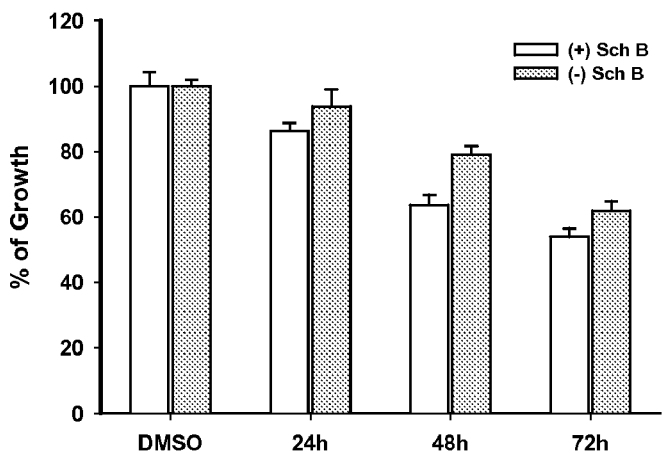
Figure 2B:
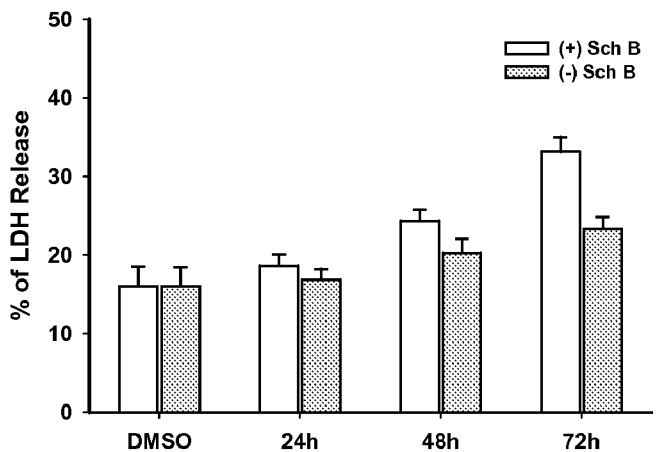

Results (+) Schisandrin B treatment also caused a dose-dependent cytotoxic effect, with the percentage of cell death being 11% at 100 μM (FIG. 2a). The differential cytotoxicity between (−) Schisandrin B and (+) Schisandrin B was confirmed by treating the cells with the drug at 100 μM for increasing periods of time up to 72 h. (−) Schisandrin B showed a lower toxicity, as assessed by the three parameters, than that of (+) Sch B (FIG. 2b). In FIG. 2b, values given are mean±S.E.M., with n=3.

Example 6

Effects of (−) Schisandrin B on Myocardial Mitochondria Functional Ability and Glutathione Antioxidant Status in Young Male and Female Rats: Protection Against Ischemia-Reperfusion Injury Methods Animal Pretreatment Male/Female adult Sprague-Dawley rats (~10 weeks old) were maintained under a 12-h dark/light cycle at about 22° C. and allowed food and water ad libitum. Animals were randomly divided into groups, with at least 5 animals in each. In the pretreatment groups, rats were treated intragastrically with (−) Schisandrin B at a daily dose of 1 or 10 mg/kg for 35 days. Control animals received oil only (10 ml/kg). Twenty-four hours following the last dosing, hearts were isolated from control or drug-pretreated rats and then subjected to Langendorff perfusion as described below.

Isolated-Perfused Rat Heart

The heart was excised quickly and immediately immersed in ice-cold and heparinized (50 unit/ml) saline. The aorta was cannulated and then transferred to a warm and moistured chamber of the perfusion apparatus. The heart was retrogradely perfused according to Langendorff method as described (Yim and Ko 1999).

Myocardial Ischemia-Reperfusion (I-R)

After an initial 30-min of perfusion for equilibration, the isolated heart was subjected to a 40-min period of 'no-flow' global ischemia followed by 20 min of reperfusion. Coronary effluent was collected in 1-min fractions at increasing time intervals during the course of equilibration and reperfusion. The fractions were immediately put on ice until assay for lactate dehydrogenase (LDH) activity. The extent of LDH leakage during the reperfusion period, an indirect index of myocardial injury, was estimated by computing the area under the curve of the graph plotting the percent LDH activity (with respect to the mean pre-ischemic value measured during the equilibration period) against the reperfusion time (1-20 min), as described (Yim and Ko 1999). Immediately after the I-R procedure, heart ventricular tissue samples were obtained for biochemical analysis.

Preparation of Mitochondrial Fractions

Myocardial tissue samples were rinsed with ice-cold isotonic buffer (50 mM Tris, 0.32 M sucrose, 1 mM $Na_2EDTA$, 0.2 mg/ml soybean trypsin inhibitor, 0.2 mg/ml bacitracine, 0.16 mg/ml benzamidine). Tissue homogenates were prepared by homogenizing 0.8 g of myocardial tissue in 8 ml ice-cold isotonic buffer and the homogenates were used for the preparation of mitochondrial fractions by differential centrifugation, as described in Chiu and Ko (2004). The mitochondrial pellets were resuspended in 1.5 ml of isotonic buffer containing 150 μl of 2 mg/ml soybean trypsin inhibitor and constituted the mitochondrial fractions.

Biochemical Analysis

Myocardial mitochondrial ATP generation capacity was measured by incubating 200 μl of nucleus-free tissue homogenate with 200 μl of substrate solution (containing 100 mM glutamate and 34 mM malate) and 20 μl ADP (2.3 mM) for 10 min at 37° C., and the ATP level were measured using an assay kit from Sigma Chemical Co. (St. Louis, Mo., USA). LDH activity was spectrophotometrically measured as described (Yim and Ko 1999).

Aliquots (500 μl) of mitochondrial fractions were taken for measuring mitochondrial GSH level by HPLC methods, using GSH as standards, respectively, as described (Chiu et al 2002). Aliquots (400 μl) of mitochondrial fractions were mixed with 933 μl Triton X-100 solution (0.3%, v/v, in isotonic buffer) and sonicated for 2 min on ice. The mixtures were then subjected to measurements of mitochondrial glutathione reductase (GRD), Se-glutathione peroxidase (GPX) and glutathione S-transferases (GST) activities by spectrophotometric methods, as described in Chiu et al. (2002).

Statistical Analysis

Data obtained from animal experiments were analyzed by one-way ANOVA followed by Duncan's multiple range test to detect the inter-group difference. Significant difference was determined when $p<0.05$.

Results

Chronic (−) Schisandrin B treatment caused an enhancement in myocardial functional status in both male and female rats, as evidenced by the dose-dependent increase in ATP generation, with the stimulatory effect on male rats being more prominent (Table 4a). (−) Schisandrin B treatment also enhanced the mitochondrial glutathione antioxidant status in male and female rats, as indicated by dose-dependent increases in GSH level and glutathione antioxidant enzyme activities, with the stimulatory effect being comparable between male and female rats (Table 4a).

The beneficial effect of (−) Schisandrin B treatment became more apparent after the I-R challenge. While the male hearts were more susceptible to I-R injury, (−) Schisandrin B pretreatment produced a dose-dependent protection against myocardial I-R injury, as evidenced by the decrease in the extent of LDH leakage, with the degree of protection being comparable between male and female rats (Table 4b).

TABLE 4a

| | Mitochondrial Functional Status ATP Generation ($\mu$mol/min/mg protein) | Mitochondrial Glutathione Antioxidant Status | | | |
|---|---|---|---|---|---|
| | | GSH (nmol/mg protein) | GPX (mU/mg Protein) | GRD (mU/mg protein) | GST (mU/mg protein) |
| MALE | | | | | |
| Control (−) Sch B | 2.80 ± 0.75 | 11.6 ± 0.37 | 52.3 ± 1.07 | 5.35 ± 0.41 | 10.1 ± 0.61 |
| 1 mg/kg | 5.58 ± .19[a] (99%) | 18.1 ± 1.06[a] (56%) | 77.3 ± 3.78[a] (48%) | 6.76 ± 0.29 (26%) | 12.8 ± 0.10 (65%) |
| 10 mg/kg | 6.74 ± 0.37[a] (141%) | 23.8 ± 1.10[a] (105%) | 83.7 ± 2.12[a] (60%) | 7.59 ± 0.13[a] (42%) | 14.5 ± 0.36[a] (83%) |
| FEMALE | | | | | |
| Control (−) Sch B | 3.25 ± 0.19 | 10.4 ± 0.41 | 51.1 ± 4.17 | 4.69 ± 0.15 | 11.1 ± 0.51 |
| 1 mg/kg | 4.11 ± 0.19[b] (26%) | 17.3 ± 1.11[b] (60%) | 73.2 ± 4.98[b] (43%) | 6.30 ± 0.37[b] (34%) | 14.1 ± 0.58[b] (37%) |
| 10 mg/kg | 5.79 ± 0.37[b] (78%) | 21.6 ± 0.38[b] (107%) | 78.3 ± 2.94[b] (53%) | 8.02 ± 0.55[b] (71%) | 16.9 ± 0.90[b] (63%) |

Animals were orally treated with (−) Sch B at the indicated daily dose for 35 days.
Myocardial mitochondrial reduced glutathione (GSH) level and Se-glutathione peroxidase (GPX), glutathione reductase (GRD) and glutathione S-transferases (GST) activities were measured.
Values given are mean ± S.E.M., with n = 5.
The number in the parentheses is the percent increase when compared with the respective untreated control.
[a]significantly different from the male control;
[b]significantly different from the female control TABLE 4b

| | LDH Leakage (AU) |
|---|---|
| NON-I-R | |
| MALE | |
| Control | 832 ± 20.6 |
| (−) Sch B | |
| 1 mg/kg | 804 ± 18.0 |
| 10 mg/kg | 820 ± 13.8 |
| FEMALE | |
| Control | 803 ± 8.15 |
| (−) Sch B | |
| 1 mg/kg | 776 ± 22.1 |
| 10 mg/kg | 813 ± 14.0 |
| I-R | |
| MALE | |
| Control | 5366 ± 349 (5.4-fold) |
| (−) Sch B | |
| 1 mg/kg | 3638 ± 125[a] (*37%*) |
| 10 mg/kg | 2775 ± 55.8[a] (*57%*) |
| FEMALE | |
| Control | 3831 ± 127 (4.7-fold) |
| (−) Sch B | |
| 1 mg/kg | 2861 ± 70.6[b] (*31%*) |
| 10 mg/kg | 2023 ± 83.1[b] (*60%*) |

Values given are mean ± S.E.M., with n = 5.
The non-italicized number in parentheses is the number of fold increase when compared with the respective control.
The italicized number in parentheses is the percent protection when compared with the respectively unpretreated control.
[a]significantly different from the male control;
[b]significantly different form the female control

Example 7

Effects of (−) Schisandrin B on Myocardial Mitochondrial Functional Ability and Glutathione Antioxidant Status in Old Male and Female Rats: Protection Against Ischemia-Reperfusion Injury Methods Aged male and female rats (~12 months old) were administered with liposome-encapsulated (−) Schisandrin B in drinking water for 35 days, with the daily dose estimated to be 10 mg/kg.

Animal Pretreatment

Male/Female adult Sprague-Dawley rats (~12 months old) were maintained under a 12-h dark/light cycle at about 22° C. and allowed food and water ad libitum. Animals were randomly divided into groups, with at least 5 animals in each. In the pretreatment groups, rats were treated with liposome-encapsulated (−) Schisandrin B in drinking water for 35 days, with the estimated daily dose of 10 mg/kg. Control animals received empty liposomes-containing drinking water. Twenty-four hours following the last dosing, hearts were isolated from control or drug-pretreated rats and then subjected to Langendorff perfusion as described below.

Isolated-Perfused Rat Heart

The heart was excised quickly and immediately immersed in ice-cold and heparinized (50 unit/ml) saline. The aorta was cannulated and then transferred to a warm and moistured chamber of the perfusion apparatus. The heart was retrogradely perfused according to Langendorff method as described (Yim and Ko 1999).

Myocardial Ischemia-Reperfusion (I-R)

After an initial 30-min of perfusion for equilibration, the isolated heart was subjected to a 40-min period of 'no-flow' global ischemia followed by 20 min of reperfusion. Coronary effluent was collected in 1-min fractions at increasing time intervals during the course of equilibration and reperfusion. The fractions were immediately put on ice until assay for lactate dehydrogenase (LDH) activity. The extent of LDH leakage during the reperfusion period, an indirect index of myocardial injury, was estimated by computing the area under the curve of the graph plotting the percent LDH activity (with respect to the mean pre-ischemic value measured during the equilibration period) against the reperfusion time (1-20 min), as described (Yim and Ko 1999). Immediately after the I-R procedure, heart ventricular tissue samples were obtained for biochemical analysis.

Preparation of Mitochondrial Fractions

Myocardial tissue samples were rinsed with ice-cold isotonic buffer (50 mM Tris, 0.32 M sucrose, 1 mM $Na_2EDTA$, 0.2 mg/ml soybean trypsin inhibitor, 0.2 mg/ml bacitracine, 0.16 mg/ml benzamidine). Tissue homogenates were prepared by homogenizing 0.8 g of myocardial tissue in 8 ml ice-cold isotonic buffer and the homogenates were used for the preparation of mitochondrial fractions by differential centrifugation, as described in Chiu and Ko (2004). The mitochondrial pellets were resuspended in 1.5 ml of isotonic buffer containing 150 μl of 2 mg/ml soybean trypsin inhibitor and constituted the mitochondrial fractions.

Biochemical Analysis

Myocardial mitochondrial ATP generation capacity was measured by incubating 200 μl of nucleus-free tissue homogenate with 200 μl of substrate solution (containing 100 mM glutamate and 34 mM malate) and 20 μl ADP (2.3 mM) for 10 min at 37° C., and the ATP level were measured using an assay kit from Sigma Chemical Co. (St. Louis, Mo., USA). LDH activity was spectrophotometrically measured as described (Yim and Ko 1999).

Aliquots (500 μl) of mitochondrial fractions were taken for measuring mitochondrial GSH level by HPLC methods, using GSH as standards, respectively, as described (Chiu et al 2002). Aliquots (400 μl) of mitochondrial fractions were mixed with 933 μl Triton X-100 solution (0.3%, v/v, in isotonic buffer) and sonicated for 2 min on ice. The mixtures were then subjected to measurements of mitochondrial glutathione reductase (GRD), Se-glutathione peroxidase (GPX) and glutathione S-transferases (GST) activities by spectrophotometric methods, as described in Chiu et al. (2002).

Statistical Analysis

Data obtained from animal experiments were analyzed by one-way ANOVA followed by Duncan's multiple range test to detect the inter-group difference. Significant difference was determined when $p<0.05$.

Results (−) Schisandrin B treatment enhanced the myocardial mitochondrial functional ability in old male and female rats, as evidenced by the increase in ATP generation, with the degree of stimulation being more prominent in female rats (Table 5a). (−) Schisandrin B treatment also enhanced the myocardial mitochondrial glutathione antioxidant status, as indicated by increases in GSH level and some of the glutathione antioxidant enzyme activities, with the stimulatory effect on male rats being more prominent (Table 5a).

While there were no apparent difference in the susceptibility to I-R injury between the hearts prepared from old male and female rats, (−) Schisandrin B pretreatment protected against I-R injury in old male and female hearts, as evidenced by the decrease in LDH leakage, with the degree of protection being comparable between male and female rats (Table 5b).

TABLE 5a

| | Mitochondrial Functional Status ATP | Mitochondrial Glutathione Antioxidant Status | | | |
|---|---|---|---|---|---|
| | Generation (μmol/min/mg protein) | GSH (nmol/mg protein) | GPX (mU/mg Protein) | GRD (mU/mg protein) | GST (mU/mg protein) |
| MALE | | | | | |
| Control (−) Sch B | 3.38 ± 0.10 | 3.52 ± 0.22 | 45.5 ± 2.04 | 2.67 ± 0.06 | 16.2 ± 0.26 |
| 10 mg/kg | 3.75 ± 0.06 (11%) | 4.43 ± 0.09[a] (265%) | 52.2 ± 0.72[a] (15%) | 3.72 ± 0.29[a] (39%) | 17.5 ± 0.76 |

TABLE 5a-continued

| | Mitochondrial Functional Status ATP | Mitochondrial Glutathione Antioxidant Status | | | |
|---|---|---|---|---|---|
| | Generation (μmol/min/mg protein) | GSH (nmol/mg protein) | GPX (mU/mg Protein) | GRD (mU/mg protein) | GST (mU/mg protein) |
| FEMALE | | | | | |
| Control (−) Sch B | 3.00 ± 0.24 | 5.19 ± 0.10 | 46.8 ± 3.62 | 5.02 ± 0.71 | 11.2 ± 1.00 |
| 10 mg/kg | 4.43 ± 0.10[b] (48%) | 6.80 ± 0.28b (31%) | 44.6 ± 4.29 | 5.65 ± 0.65 (13%) | 14.0 ± 0.45[b] |

Animals were treated with (−) Sch B in drinking water at the indicated daily dose for 15 days.
Myocardial mitochondrial reduced glutathione (GSH) level and Se-glutathione peroxidase (GPX), glutathione reductase (GRD) and glutathione S-transferases (GST) activities were measured.
Values given are mean ± S.E.M., with n = 5.
The number in the parentheses is the percent increase when compared with the respective untreated control.
[a]significantly different from the male control;
[b]significantly different from the female control TABLE 5b

| | LDH Leakage (AU) |
|---|---|
| NON-I-R | |
| MALE | |
| Control | 645 ± 98.0 |
| (−) Sch B | |
| 10 mg/kg | 570 ± 66.8 |
| FEMALE | |
| Control | 782 ± 21.3 |
| (−) Sch B | |
| 10 mg/kg | 611 ± 49.7 |
| I-R | |
| MALE | |
| Control | 5540 ± 314 (7.6-fold) |
| (−) Sch B | |
| 10 mg/kg | 2426 ± 219[a] (62%) |
| FEMALE | |
| Control | 6887 ± 250 (7.8-fold) |
| (−) Sch B | |
| 10 mg/kg | 4534 ± 86.5[b] (56%) |

Values given are mean ± S.E.M., with n = 5.
The non-italicized number in parentheses is the number of fold increase when compared with the respective control.
The italicized number in parentheses is the percent protection when compared with the respective unpretreated control.
[a]significantly different from the male I-R control;
[b]significantly different from the female I-R control Example 8

Effects of Chronic (−) Schisandrin B Treatment on Mitochondrial Functional Ability and Antioxidant Status as Well as Tissue Heat Shock Protein Expression in Various Tissues in Young Female Rats Methods Drug Treatment Female Sprague-Dawley rats (8 weeks old) were maintained under a 12-h dark/light cycle at about 22° C. and allowed food and water ad libitum. Drug treated animals received a daily bolus dose of (−) Schisandrin B, α-lipoic acid (α-LA) or α-tocopherol (α-Toc) at 10, 5 and 70 mg/kg, respectively, for 15 days. The dosages were determined with reference to the equivalent amount of crude herb prescribed for human or the daily recommended intake in health supplements. The control animals received olive oil only. Twenty-four hours after the last dose, the pentobarbital-anesthetized animals were sacrificed by cardiac excision, and brain, heart, liver and skeletal muscle tissues were obtained.

Preparation of Mitochondrial Fractions

Tissue samples (brain, heart, liver, and skeletal muscle) were rinsed with ice-cold isotonic buffer (50 mM Tris, 0.32 M sucrose, 1 mM $Na_2EDTA$, 0.2 mg/ml soybean trypsin inhibitor, 0.2 mg/ml bacitracine, 0.16 mg/ml benzamidine). Tissue homogenates were prepared by homogenizing 0.8 g of myocardial tissue in 8 ml ice-cold isotonic buffer and the homogenates were used for the preparation of mitochondrial fractions by differential centrifugation, as described in Chiu and Ko (2004). The mitochondrial pellets were resuspended in 1.5 ml of isotonic buffer containing 150 μl of 2 mg/ml soybean trypsin inhibitor and constituted the mitochondrial fractions.

Biochemical Analysis

Mitochondrial ATP generation capacity was measured by incubating 200 μl of nucleus-free tissue homogenate with 200 μl of substrate solution (containing 100 mM glutamate and 34 mM malate) and 20 μl ADP (2.3 mM) for 10 min at 37° C., and the ATP level were measured using an assay kit from Sigma Chemical Co. (St. Louis, Mo., USA). Aliquots (500 μl) of mitochondrial fractions were taken for measuring mitochondrial GSH level by HPLC methods, using GSH as standards, respectively, as described (Chiu et al 2002). Aliquots (400 μl) of mitochondrial fractions were mixed with 933 μl Triton X-100 solution (0.3%, v/v, in isotonic buffer) and sonicated for 2 min on ice. The mixtures were then subjected to measurements of mitochondrial glutathione reductase (GRD), Se-glutathione peroxidase (GPX) and glutathione S-transferases (GST) activities by spectrophotometric methods, as described in Chiu et al. (2002).

Hsp25 and Hsp70 levels was estimated by Western blot analysis using specific antibodies (anti-Hsp25, catalog # SPA-801; anti-Hsp70, catalog # SPA-812) from StressGen (Vancouver, BC, Canada) following SDS-PAGE analysis of the nuclear-free tissue homogenates, using a separating gel of 10% acrylamide as described in Ip et. al. (2001). Hsp25/27 and Hsp70 (human recombinant proteins from StressGen) and actin (bovine muscle from Sigma) were used as markers (−) Schisandrin B treatment also increased the Hsp70 level in all tissues tested, with the extent of stimulation in brain tissue being more prominent. No detectable changes in Hsp25 level were observed in all tissues (Table 6b).

TABLE 6a

| | Mitochondrial Functional Status ATP generation | Mitochondrial Antioxidant Status | | | | |
|---|---|---|---|---|---|---|
| | | GSH | GRD | GPX | GST | α-Toc |
| BRAIN | | | | | | |
| Control | 100 ± 2 | 100 ± 5 | 100 ± 4 | 100 ± 6 | 100 ± 5 | 100 ± 3 |
| (−) Sch B | 143 ± 2** | 147 ± 4** | 150 ± 9*** | 163 ± 9** | 143 ± 4*** | 141 ± 7** |
| α-LA | 72 ± 4* | 93 ± 2 | 131 ± 5** | 126 ± 9** | 103 ± 3 | 110 ± 6 |
| α-Toc | 62 ± 8* | 119 ± 6* | 153 ± 10** | 121 ± 12 | 121 ± 5* | 139 ± 9* |
| HEART | | | | | | |
| Control | 100 ± 5 | 100 ± 10 | 100 ± 11 | 100 ± 6 | 100 ± 6 | 100 ± 3 |
| (−) Sch B | 131 ± 4** | 159 ± 2*** | 163 ± 6*** | 143 ± 7*** | 161 ± 5** | 160 ± 13*** |
| α-LA | 68 ± 9 | 103 ± 4 | 144 ± 11* | 105 ± 9 | 119 ± 6* | 111 ± 4* |
| α-Toc | 95 ± 12 | 152 ± 9* | 243 ± 20** | 130 ± 10* | 159 ± 7** | 151 ± 5** |
| LIVER | | | | | | |
| Control | 100 ± 9 | 100 ± 10 | 100 ± 1 | 100 ± 8 | 100 ± 3 | 100 ± 13 |
| (−) Sch B | 134 ± 5* | 175 ± 5*** | 161 ± 10*** | 135 ± 3*** | 154 ± 4*** | 167 ± 14** |
| α-LA | 77 ± 5* | 117 ± 2 | 143 ± 8** | 159 ± 10** | 112 ± 3* | 124 ± 13 |
| α-Toc | 83 ± 8 | 133 ± 11 | 161 ± 5*** | 169 ± 14** | 128 ± 3* | 214 ± 31** |
| SKELETAL MUSCLE | | | | | | |
| Control | 100 ± 24 | 100 ± 5 | 100 ± 6 | 100 ± 8 | 100 ± 6 | 100 ± 2 |
| (−) Sch B | 105 ± 41 | 137 ± 1** | 166 ± 4*** | 125 ± 5* | 171 ± 10*** | 178 ± 13** |
| α-LA | 101 ± 1 | 154 ± 12* | 123 ± 12 | 117 ± 5 | 171 ± 19*** | 147 ± 14* |
| α-Toc | 80 ± 8 | 153 ± 6** | 149 ± 8** | 136 ± 7** | 176 ± 13*** | 189 ± 11*** |

Animals were treated with (−) Sch B, α-lipoic acid (α-LA) or α-tocopherol (α-Toc) at a daily dose of 10, 5 and 70 mg/kg, respectively, for 15 days.
Myocardial mitochondrial reduced glutathione (GSH) level and Se-glutathione peroxidase (GPX), glutathione reductase (GRD) and glutathione S-transferases (GST) activities were measured.
Data were expressed as percent control.
Values given are mean ± S.E.M., with n = 5.
The number in the parentheses is the percent increase when compared with the respective untreated control.
*$p < 0.05$,
**$p < 0.005$ and
***$p < 0.0005$ when compared with the respected untreated control.

for reference. The immuno-stained protein bands were revealed by alkaline phosphatase reaction. All immuno-blots were analyzed by densitometry, and the amounts (arbitrary units) of Hsp were normalized with reference to actin levels (arbitrary units) in the sample.

Results (−) Sch B treatment enhanced the mitochondrial functional status in brain, heart and liver tissue, as evidenced by the increase in ATP generation capacity (TABLE 6A). No detectable change in ATP generation was observed in skeletal muscle tissue (TABLE 6 A). (−) Schisandrin B treatment enhanced the mitochondrial antioxidant status in all tissues tested, as indicated by increases in GSH level and glutathione antioxidant enzyme activities as well as α-tocopherol level (Table 6a).

Antioxidant treatment using α-LA or α-Toc also enhanced the mitochondrial antioxidant status in various tissues to varying degrees. However, both α-LA and α-Toc treatment decreased, in contrast to the enhancing effect of (−) Schisandrin B, the mitochondrial ATP generation capacity in various tissues.

TABLE 6b

| | Heat Shock Protein Level (AU) | |
|---|---|---|
| | Hsp70 | Hsp25 |
| BRAIN | | |
| Control | 0.28 ± 0.02 | 0.10 ± 0.02 |
| (−) Sch B | 0.49 ± 0.05* (77%) | 0.16 ± 0.01 |
| HEART | | |
| Control | 0.61 ± 0.04 | 0.71 ± 0.03 |
| (−) Sch B | 0.71 ± 0.03* (17%) | 0.77 ± 0.05 |
| LIVER | | |
| Control | 0.47 ± 0.04 | 0.35 ± 0.02 |
| (−) Sch B | 0.69 ± 0.001*** (45%) | 0.41 ± 0.02 |

TABLE 6b-continued

| | Heat Shock Protein Level (AU) | |
|---|---|---|
| | Hsp70 | Hsp25 |
| SKELETAL MUSCLE | | |
| Control | 0.44 ± 0.01 | 0.54 ± 0.04 |
| (−) Sch B | 0.69 ± 0.07*** (57%) | 0.59 ± 0.03 |

Values given are mean ± S.E.M., with n = 5.
The number in the parentheses is the percent increase when compared with the respective untreated control.
*$p < 0.05$,
**$p < 0.005$ and
***$p < 0.0005$ when compared with the respected untreated control Example 9

Preparation of Sport-Qi (SQ) Liquid

Preparation of Saponin-Containing Extract (SQ-I)

300 gram *Panax ginseng* Meyer and 900 gram *Ophiopogon japonica* Ker-Gawl powders were extracted by water (3L, adjusted to pH 3.2 by adding citric acid) for 2 h under boiling and reflux conditions. The extraction procedure was repeated twice. The pooled extract was concentrated by rota-vaporation under reduced pressure to 1 L. The concentrated extract was precipitated by adding 2.8 L of 95% ethanol to make up a final concentration of ethanol of 70%. After removing the precipitates by filtration, the filtrate was concentrated by rota-vaporation under reduced pressure to obtain a paste, which was then dissolved in 750 ml water. This is the SQ-1. The total saponin content is determined using ginsenoside Re as standard.

Preparation of Lignan-Containing Extract (SQ-II)

900 gram of *Schisandra* fruit powder was extracted by $CO_2$ supercritical fluid at 60° C. and 7500 psi. The restrictor was kept at 80° C., and the static extraction time was set at 5 min. The flow rate was 2 ml/min, and the dynamic extraction was maintained for 30 min. In each extraction, the extract was continuously collected in methanol during the dynamic extraction. Ethanol may be used in place of methanol to collect the extract when preparing a preparation for consumption or administration to a subject. The total lignans and (−) Schisandrin B content were measured by HPLC method.

Reconstitution of Sport-Qi (SQ) Liquid

SQ-I (750 ml) was mixed with SQ-II (67 g). The pH of the mixture is adjusted to 7 by the addition of diluted hydrochloric acid. This is SQ liquid.

On a concentration basis, the composition of SQ may vary as follows (Table 7).

TABLE 7

| | (mg/ml) | Preferred composition (mg/ml) |
|---|---|---|
| Total saponins | 6-15 | 6.0 |
| Total lignans | 1.0-2.0 | 1.0 |
| (−) Schisandrin B | 0.2-0.4 | 0.2 |

Example 10

Chemical Analysis of Sport-Qi

Total Saponins Content

The total saponin content of SQ-I was measured by the method of Hiai et al. (1975), using ginsengoside Re as standard.

Total Lignans and (−) Schisandrin B Content

Total lignans and (−) Schisandrin B content of SQII was measured by an HPLC method, using $C_{18}$ NovaPak column (3.9 mm×150 mm). The mobile phase was 65% methanol (v/v, in $H_2O$) and eluted at 1 ml/min. The total lignan content was estimated using a (−) Schisandrin B standard.

Example 11

(−) Schisandrin B Treatment Reverses the Mitochondrial Changes in Antioxidant Status with Aging Materials and Methods Animal Treatment Young adult (8-10 week-old) and middle-aged (12-14 month-old retired breeder) female Sprague-Dawley rats were maintained under a 12-h dark/light cycle at about 22° C. and allowed food and water ad libitum. Experimental protocols were approved by the Research Practice Committee at the Hong Kong University of Science & Technology, Hong Kong. Animals were randomly divided into groups, with 5 animals in each. In the treatment groups, rats were intragastrically administered with Sch B (dissolved/suspended in olive oil) at a daily dose of 10 mg/kg for 15 days. The daily dose is approximated to 1.14 mg/kg for humans after adjusting the inter-species difference in drug distribution in the body. Untreated control animals received olive oil only. Twenty-four hours after the last dosing, animals were sacrificed by decapitation and the whole brain, heart ventricular, liver and skeletal muscle (hind limb) tissues were excised and subjected to biochemical analysis. To investigate the effect of (−) Sch B on myocardial ischemia-reperfusion (I-R) injury, rats were intragastrically administered with (−) Sch B at a daily dose of 10 mg/kg for 35 days. Untreated control animals received olive oil only. Twenty-four hours after the last dosing, hearts were isolated from pentobarbital-anesthetized animals and subjected to I-R experiment.

Preparation of Tissue Homogenates

Brain Homogenates

Minced whole brain tissues (~2 g) were homogenized in 10 ml of ice-cold sucrose buffer (0.25 M sucrose, 0.1 mM $Na_2EDTA$, 5 mM Tris/HCl, pH 7.4) with a Teflon-glass homogenizer at 200 rpm for 8-10 complete strokes.

Heart Homogenates

Minced heart ventricular tissues (~0.6 g) were homogenized in 10-fold (w/v) of ice-cold sucrose buffer (0.32 M sucrose, 1 mM EDTA, 50 mM Tris/HCl, pH 7.4) with a Teflon-glass homogenizer at 4,000 rpm for 25-30 complete strokes.

Liver Homogenates

Minced liver tissues (0.6 g) were homogenized in 6 ml of ice-cold sucrose buffer (0.25 M sucrose, 0.1 mM $Na_2EDTA$, 5 mM Tris/HCl, pH 7.4) with a Teflon-glass homogenizer at 2,000 rpm for 8-10 complete strokes.

Skeletal Muscle Homogenates

Minced skeletal muscle tissues (~2.5 g) were mixed with 10 ml collagenase solution (0.075% (w/v) in buffer), and the mixtures were incubated at 4° C. for 20 min. The digested tissue is mixtures were centrifuged at 600×g at 4° C. for 20 min. After removing the supernatant, the digested tissues were mixed with 20 ml of ice-cold homogenizing buffer (100 mM KCl, 50 mM MOPS, 10 mM EGTA, pH 7.2) and subjected to a burst of Polytron homogenizer at 9,500 rpm for 10 sec, which was followed by a further homogenization with a Teflon-glass homogenizer at 4,000 rpm for 25-30 complete strokes.

Preparation of Mitochondrial Fractions

Mitochondrial pellets were prepared from tissue homogenates by centrifugation at 800×g at 4° C. for 30 min, with purity being determined by measuring the relative specific activities of succinate dehydrogenase and lactate dehydrogenase (LDH) in the supernatant and mitochondrial pellet. Mitochondrial pellets were then resuspended in 1 ml of the respective homogenizing buffer used for various tissues and constituted the mitochondrial fractions. The protein concentration of mitochondrial fractions was determined using a Bio-Rad protein assay kit.

Antioxidant Levels and Enzyme Activities

Aliquots (200 µl) of mitochondrial fractions were used for measuring mitochondrial glutathione (GSH) and α-tocopherol (α-TOC) levels by an enzymatic method and HPLC method, respectively, using GSH and α-TOC as standards. Se-glutathione peroxidase (GPX) activity was measured. Mn-superoxide dismutase (SOD) activity was measured by monitoring the oxidation of cytochrome c caused by superoxide radicals generated from the xanthine oxidase-xanthine reaction.

Mitochondrial Reactive Oxidant Species (ROS) Generation

An aliquot (50 µl) of mitochondrial fraction (50 µg protein/ml) and 60 µl of DCFDA solution (17.5 µM in incubation buffer) were added into wells of a black micro-titer plate. The mixture was incubated at 37° C. for 10 min under dark condition in a Victor$^2$ Multi-Label Counter. After the incubation, 50 µl of incubation buffer (0. 1 mM EGTA, 5 mM $KH_2PO_4$, 3 mM $MgCl_2$, 145 mM KCl, 30 mM Hepes, pH 7.4) and 50 µl of substrate solution (20 mM pyruvate and 10 mM malate) were added. Fluorescence intensity (excitation: 485 nm and emission: 535 nm) of the reaction mixture was monitored every 5 min for 60 min. The mitochondrial ROS generation was reflected by the fluorescence intensity of the sample after subtracting the value of a blank sample containing incubation buffer, substrate solution and DCFDA. The extent of ROS generation over the 60-min period of incubation was estimated by computing the area under the curve (AUC) of the graph plotting fluorescent intensity against time (0-60 min) and expressed in arbitrary unit Mitochondrial Permeability Transition (MPT)

Tissue homogenates were prepared as described above. The homogenates were centrifuged at 600 g for 10 min. After collecting the supernatants, the pellets were resuspended with the same volume of ice-cold homogenizing buffer (without various protease inhibitors) and re-centrifuged at 600 g again. The procedure was repeated twice. The pooled supernatants (a total of 4 volumes) were centrifuged at 8,000 g for 30 min, and the mitochondrial pellets were collected. The mitochondrial pellets were then washed with the same volume of ice-cold sucrose buffer (50 mM Tris, pH 7.4) containing 220 mM mannitol, 140 mM sucrose, 2 mM Hepes-KOH, and the mixtures were centrifuged at 8,000 g for 30 min. The washing procedure was repeated twice. The mitochondrial pellets were resuspended in 0.5-1.0 ml of ice-cold sucrose buffer and constituted the mitochondrial fractions. An aliquot (1.6 ml) of mitochondrial sample (0.5 mg protein/ml) was prepared by mixing mitochondrial fraction with incubation buffer (125 mM sucrose, 65 mM KCl, 10 mM Hepes, pH 7.2, 5 mM succinate (freshly prepared) and 5 µM rotenone (freshly prepared). Aliquots (200 µl) of mitochondrial sample were mixed with 10 µl of cyclosporin A (5 µM in 0.5% ethanol final concentration) or incubation buffer. The mixtures were incubated at 30° C. for 5 min. An aliquot (10 µl) of calcium chloride solution (1 µM final concentration) was then added, and the mixtures were incubated at 30° C. for 5 min. Aliquots (180 µl) of the mixtures were added into 96-well micro-titer plate, and the initial absorbance of the mixtures at 520 nm was monitored for 5 min at 30° C. The swelling reaction was then started by adding 20 µl of $K_3PO_4$ (0.5 mM, pH 7.2), and the absorbance at 520 nm of the reaction mixtures was read every 2 min for 30 min at 30° C., using Victor $V^2$ Multi-Label Counter. The extent of mitochondrial swelling was estimated by computing the AUC of the declining graph plotting percent initial absorbance (100% as baseline) against time (min). The extent of MPT was estimated by subtracting the AUC with cyclosporin A from the AUC without cyclosporin A. The $Ca^{2+}$-induced MPT was obtained by subtracting the MPT value with $PO_4^{3-}$ only from that with both $Ca^{2+}$ and $PO_4^{3-}$.

Myocardial I-R Injury

The heart was excised quickly and immediately immersed in ice-cold saline containing heparin (50 unit/ml). The aorta was cannulated and then transferred to a warm and moistured chamber of the perfusion apparatus. The perfusion buffer (a modified Krebs-Henseleit bicarbonate solution (pH 7.4) containing 120 mM NaCl, 25.4 mM $NaHCO_3$, 4.8 mM NaCl, 1.2 is mM $KH_2PO_4$, 0.86 mM $MgSO_4$, 1.25 mM $CaCl_2$ and 11 mM glucose) was maintained at 37° C. and gassed with 95% $O_2$-5% $CO_2$ gas mixture. The heart was retrogradely perfused at a constant pressure of 60 mm Hg (maintained by a peristaltic pump) to give a coronary flow rate of 6-11 ml/min and a heart rate of 160-200 beats/min during the equilibration period. After an initial 30-min of perfusion for equilibration, the isolated heart was subjected to a 40-min period of 'no-flow' global ischemia. This was achieved by clamping the retrograde aortic perfusion. After ischemia, flow was restored and the heart was reperfused for a 20-min period. Coronary effluent was collected in 1-min fraction every 10 min or 1 min during the course of equilibration and reperfusion, respectively. The fractions were immediately put on ice until assay for LDH activity. The extent of LDH leakage during the reperfusion period, an indirect index of myocardial injury, was estimated by computing the AUC of the graph plotting the percent LDH activity released per min (with respect to the mean of pre-ischemic values measured during the equilibration period at 10, 20 and 30 min) against the reperfusion time (1-20 min).

Statistical Analysis

Significant difference between two groups (young adult vs. middle-aged; untreated control vs. Sch B-treated) was detected using Student's t test. Data obtained from the study on myocardial I-R injury were analyzed by one-way ANOVA followed by Duncan's multiple range test to detect inter-group difference, where $p<0.05$.

TABLE 8

| | Mitochondrial Antioxidant Components | | | |
|---|---|---|---|---|
| | GSH nmol/mg protein | α-TOC ng/mg protein | GPX | SOD |
| | | | mU/mg protein | |
| Young Adult | | | | |
| brain | 8.03 ± 0.19 | 237 ± 6.12 | 1.20 ± 0.03 | 22.7 ± 0.97 |
| heart | 3.40 ± 0.04 | 123 ± 7.20 | 3.32 ± 0.22 | 50.5 ± 2.19 |
| liver | 6.31 ± 0.10 | 88.4 ± 2.83 | 15.0 ± 1.35 | 39.6 ± 1.35 |
| skeletal muscle | 1.14 ± 0.28 | 245 ± 7.56 | 1.21 ± 0.08 | 12.6 ± 0.71 |
| Middle-Aged | | | | |
| brain | 5.13 ± 0.28** (−36) | 182 ± 6.92* (−23) | 0.78 ± 0.02*** (−35) | 16.8 ± 1.77* (−26) |
| heart | 2.72 ± 0.04*** (−20) | 95.4 ± 3.10* (−22) | 2.17 ± 0.11* (−35) | 36.8 ± 0.80* (−27) |
| liver | 5.56 ± 0.16** (−12) | 65.3 ± 1.87** (−26) | 9.54 ± 0.13* (−36) | 19.5 ± 0.95*** (−51) |
| skeletal muscle | 0.98 ± 0.02* (−14) | 174 ± 3.77*** (−29) | 1.05 ± 0.02 (−13) | 8.22 ± 0.14** (−35) |

Young adult (8-10 week-old) and middle-aged (12-14 month-old) female Sprague-Dawley rats were used in the experiment. Mitochondrial reduced glutathione (GSH) and α-tocopherol (α-TOC) levels as well as Se-glutathione peroxidase (GPX) and Mn-superoxide dismutase (SOD) activities were measured as described in Materials and methods.
Values given are mean ± S.E.M., with n = 5.
The italicized number in parentheses is the percent change with respect to values in the young adult group.
*p < 0.05;
**p < 0.01;
***p < 0.001, when compared with the young adult group, using Student's t test.

Results

Figure 1:
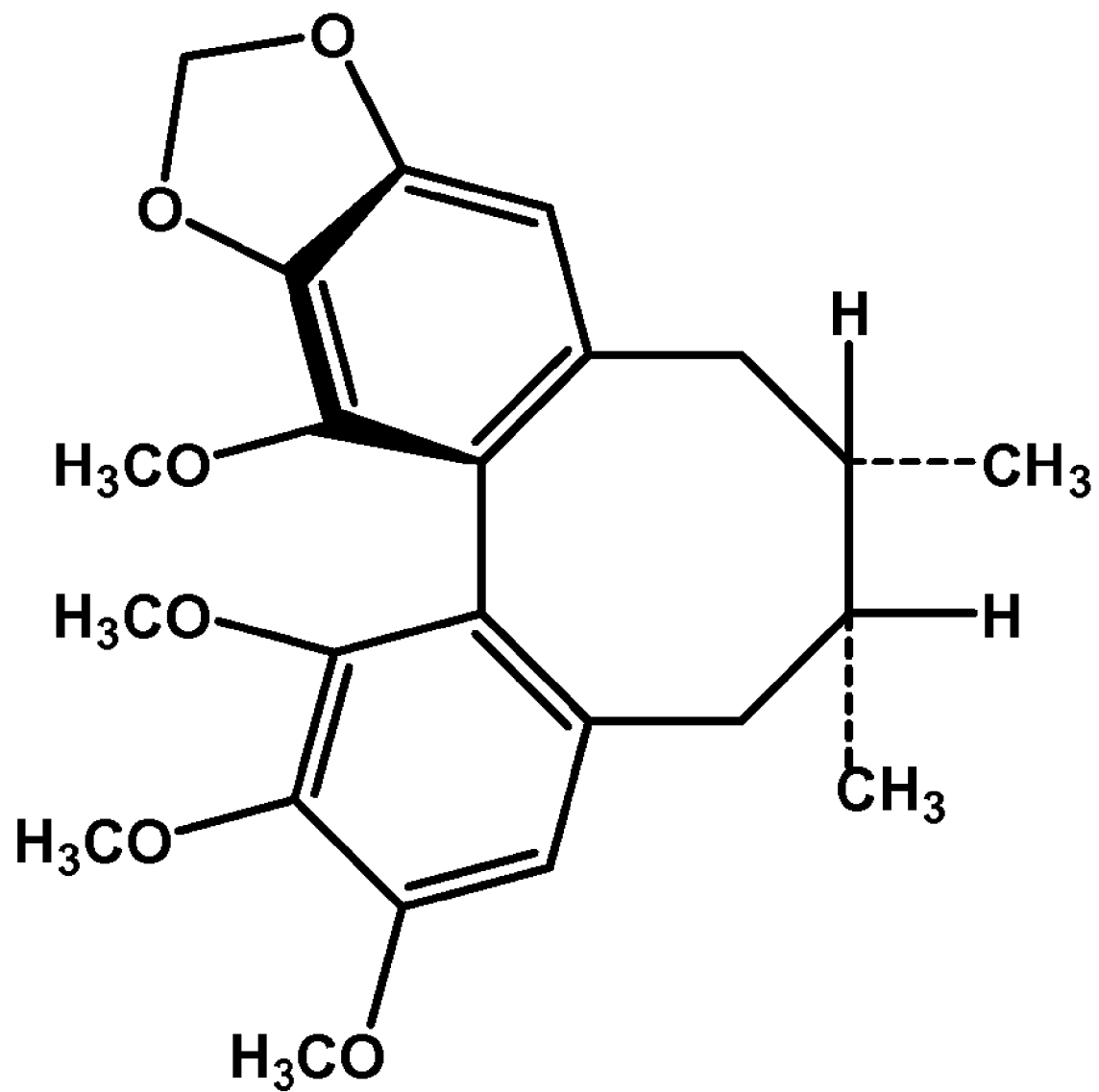
FIG. 1 illustrates the structure of (-) Schisandrin B.

Changes in Mitochondrial Antioxidant Components with Aging and the Effect of (−) Sch B Treatment Levels/activities of mitochondrial antioxidant components, namely, GSH, α-TOC, GPX and SOD, varied among tissues in young adult rats (Table 8). A descending order of the respective antioxidant level/activity among tissues is as follows: GSH, brain>liver>heart>skeletal muscle; α-TOC, brain, skeletal muscle>heart>liver; GPX, liver>heart >brain, skeletal; SOD, heart>liver>brain>skeletal muscle. Age-dependent impairment in mitochondrial antioxidant components was observed in all tissues, with the extent of decrease in level/activity of antioxidants, namely, GSH (12-36%), α-TOC (22-29%), GPX (12-36%), SOD (26-51%), varying among tissues. Chronic Sch B treatment (10 mg/kg/day×15) enhanced mitochondrial antioxidant components in various tissues of young adult rats (FIG. 1). The extent of stimulation by Sch B treatment on mitochondrial antioxidant levels/activities, namely, GSH (21-29%), α-TOC (19-34%), GPX (21-41%), SOD (19-34%), varied among tissues. The Sch B treatment also produced a parallel effect on mitochondrial antioxidant components in middle-aged rats, but to a lesser extent when compared with young adult rats, except for myocardial mitochondrial GSH level which was increased by Sch B treatment to an extent larger than that of young adult animals.

Changes in Mitochondrial ROS Generation with Aging and the Effect of (−) Sch B Treatment The extent of mitochondrial ROS generation, as assessed by in vitro measurement, varied among tissues in a descending order of brain, liver>heart>skeletal muscle (FIG. 2). An age-dependent increase in mitochondrial ROS generation was observed in all tissues, with the extent of increase (14-19%) varying among tissues. Chronic Sch B treatment suppressed the mitochondrial ROS generation to varying extents (16-38%) in all tissues. In middle-aged rats, Sch B treatment also decreased the mitochondrial ROS generation to varying degrees (11-23%) in tissues. However, the difference in liver mitochondrial ROS generation between control and (−) Sch B-treated middle-aged rats was not statistically significant.

Figure 3:
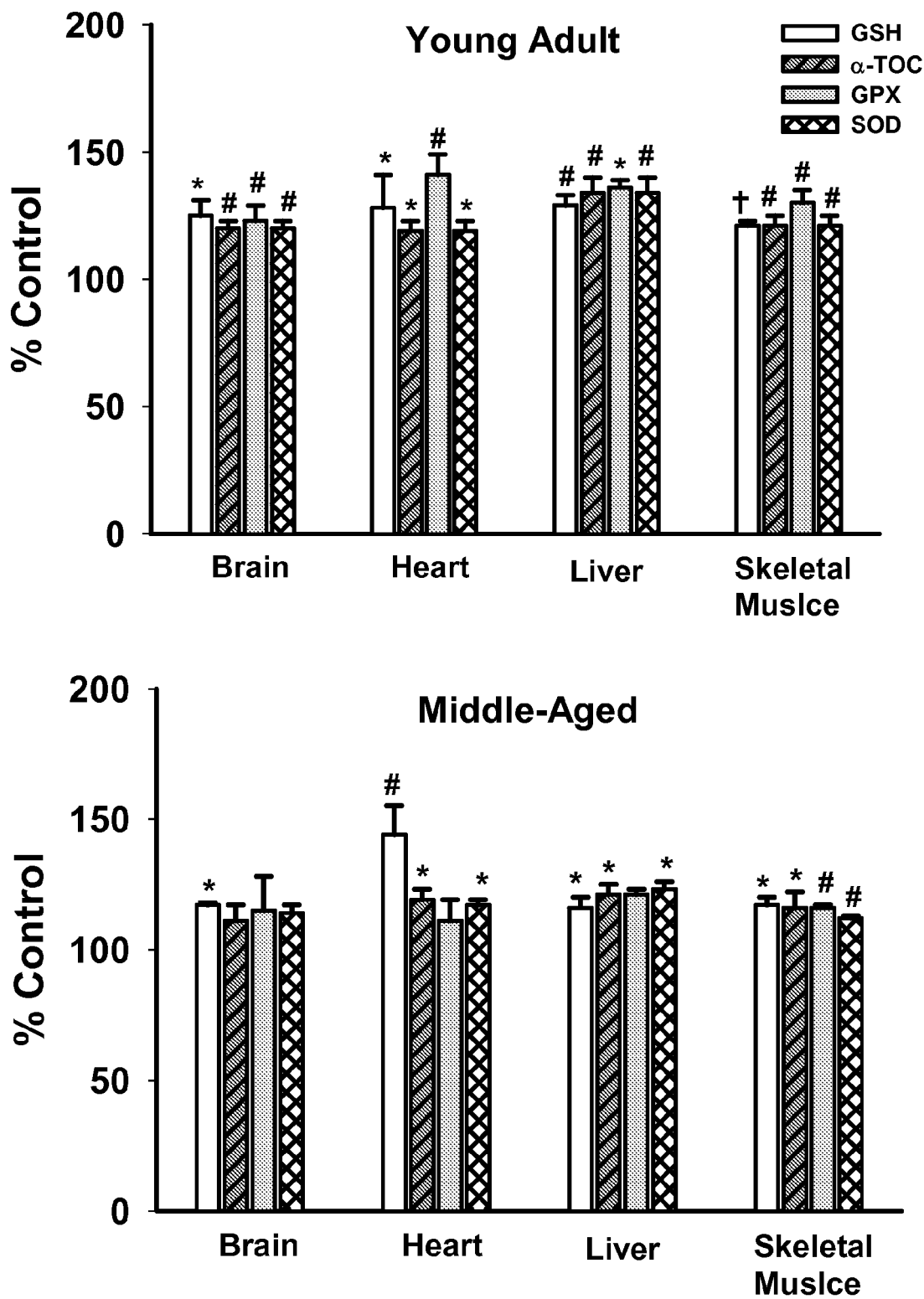
FIG. 3 depicts the effects of chronic (-) Schisandrin B (Sch B) treatment on mitochondrial antioxidant components in various tissues of young adult and middle-aged rats. Young adult and middle-aged animals were orally treated with Sch B at a daily dose of 10 mg/kg for 15 days. Mitochondrial antioxidant components were analyzed as described in Table 8. Data were expressed as percent control with respect to control (i.e. untreated) values of young adult and middle-aged animals shown in Table 1. Values given are mean±S.E.M., with n=5. * $p<0.05$; # $p<0.01$; † $p<0.001$, when compared with the respective control in young adult group, using Student's t test.

Changes in Sensitivity to $Ca^{2+}$-Induced MPT and the Effect of (−) Sch B Treatment The sensitivity to $Ca^{2+}$-induced MPT, as assessed by the extent of mitochondrial swelling, varied among tissues in a descending order of heart, liver>skeletal muscle>brain in young adult rats (FIG. 3). An age-dependent increase (50%) in the sensitivity to $Ca^{2+}$-induced MPT was observed in brain tissue only. Chronic Sch B treatment decreased the sensitivity to $Ca^{2+}$-induced MPT to varying extents (15-48%) in young adult rat tissues. In middle-aged rats, (−) Sch B treatment also decreased the sensitivity to $Ca^{2+}$-induced MPT in all tissues except that of the liver which did not show detectable change, with the extent of inhibition (15-29%) varying among tissues.

Figure 4:
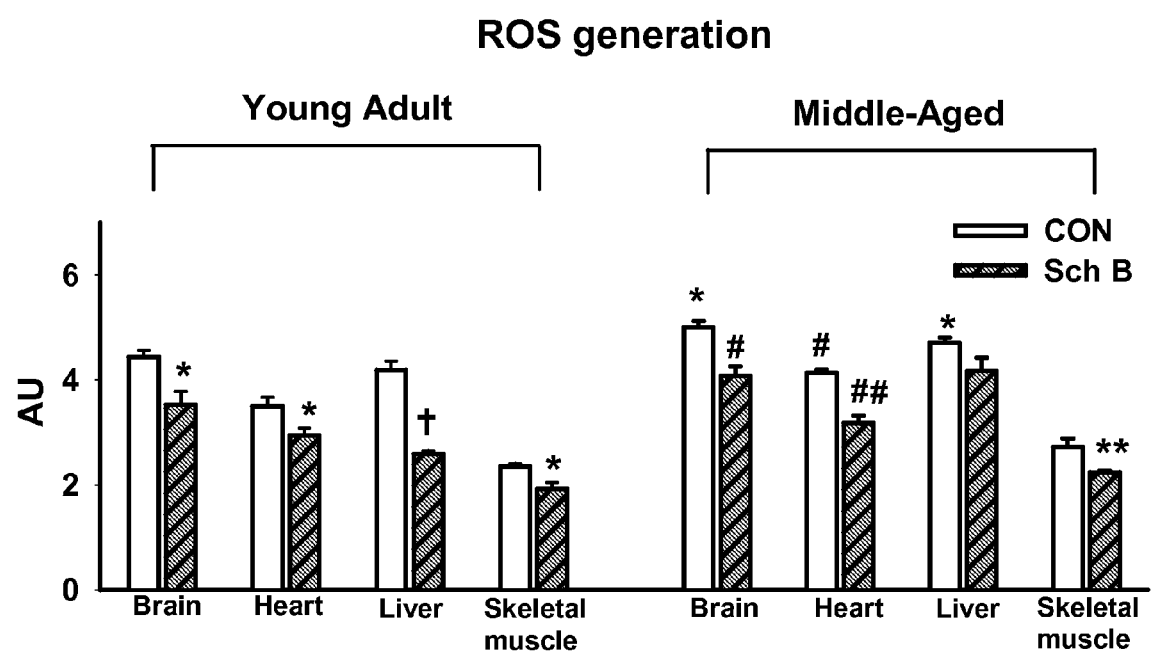
FIG. 4 illustrates the effects of chronic (-) Schisandrin B treatment on mitochondrial reactive oxygen species generation in various tissues of young and middle-aged rats. Animals were treated with Sch B as described in FIG. 3. The extent of mitochondrial reactive oxygen species (ROS) generation was measured in vitro as described in Materials and methods. Data were expressed in arbitrary unit (AU). Values given are mean±S.E.M., with n=5. * $p<0.05$; # $p<0.01$.

Changes in Susceptibility to Myocardial I-R Injury with Aging and the Effect of (−)Sch B Treatment A 40-min of ischemia followed by 20-min of reperfusion caused I-R injury, as assessed by LDH leakage, in young adult rat hearts (FIG. 4). An age-dependent increase in susceptibility to myocardial I-R injury was observed, as evidenced by the significant increase in the extent of LDH leakage (6.8-fold in young adult versus 7.8-fold in middle-aged). Chronic (−) Sch B treatment (10 mg/kg/day×35) protected against myocardial I-R injury in both young adult and middle-aged rats, with the degree of protection in young adult rats being more prominent (55% versus 36%).

SUMMARY

Age-dependent (young vs. middle age) impairment in mitochondrial antioxidant status was observed in various tissues (brain, heart, liver, skeletal muscle) in rats. Chronic (−) Sch B treatment (10 mg/kg/day×15) was able to enhance mitochondrial antioxidant status and the resistance to $Ca^{2+}$-induced mitochondrial permeability transition in an age-independent manner in various tissues of rats. The Sch B-induced enhancement of mitochondrial protective parameters in the heart was associated with the protection against myocardial ischemia-reperfusion injury in both young adult and middle-aged rats. The results suggest that chronic Sch B treatment may be beneficial for reversing the mitochondrial changes with aging.

While the foregoing invention has been described in some detail for purposes of clarity and understanding, it will be appreciated by one skilled in the art, from a reading of the disclosure, that various changes in form and detail can be made without departing from the true scope of the invention in the appended claims.

The invention claimed is:

1. A method for reducing aging-related mitochondrial antioxidant status changes in a subject, comprising administering to the subject an effective amount of a composition including isolated (−) Schisandrin B.

2. The method of claim 1, wherein the composition raises the level of at least one of glutathione and α-tocopherol in mitochondria.

3. The method of claim 1, wherein the composition increases the activity of at least one of Se-glutathione peroxidase and Mn-superoxide dismutase in mitochondria.

4. The method of claim 1, wherein the composition reduces mitochondrial reactive oxidant species generation.

5. The method of claim 1, wherein the composition reduces the sensitivity of mitochondria to $Ca^{2+}$-induced mitochondrial permeability transition.

6. The method of claim 1, wherein the subject is an animal.

* * * * *